(12) United States Patent
Debnath et al.

(10) Patent No.: US 8,299,093 B2
(45) Date of Patent: Oct. 30, 2012

(54) SMALL MOLECULE INHIBITORS OF RETROVIRAL ASSEMBLY AND MATURATION

(75) Inventors: Asim Kumar Debnath, Fort Lee, NJ (US); Hongtao Zhang, Oakland Gardens, NY (US); Francesca Curreli, Bronx, NY (US)

(73) Assignee: New York Blood Center, Inc., New York, NY (US)

( * ) Notice: Subject to any disclaimer, the term of this patent is extended or adjusted under 35 U.S.C. 154(b) by 501 days.

(21) Appl. No.: 12/536,738

(22) Filed: Aug. 6, 2009

(65) Prior Publication Data

US 2010/0035912 A1  Feb. 11, 2010

Related U.S. Application Data

(60) Provisional application No. 61/087,574, filed on Aug. 8, 2008.

(51) Int. Cl.
*A61K 31/47* (2006.01)
(52) U.S. Cl. ..................................... 514/312
(58) Field of Classification Search .................. 514/312
See application file for complete search history.

(56) References Cited

U.S. PATENT DOCUMENTS

| 2 A | 7/1836 | Goulding |
|---|---|---|
| 6,455,670 B1 | 9/2002 | van der Spoel et al. |
| 2003/0228573 A1 | 12/2003 | Summers et al. |

FOREIGN PATENT DOCUMENTS

| WO | 01/10456 A2 | 2/2001 |
|---|---|---|
| WO | 2007/008541 A2 | 1/2007 |
| WO | 2007/009541 A1 | 1/2007 |
| WO | 2007/048042 A2 | 4/2007 |
| WO | 2007/136592 A2 | 11/2007 |
| WO | 2008/113006 A1 | 9/2008 |
| WO | 2009/155064 A1 | 12/2009 |

OTHER PUBLICATIONS

STN registration file, RN 552826-02-5, 2003.*
Badawey et al. "Bezimidazole condensed ring system. IX. Potential antineoplastics. New synthesis of some pyrido [1,2-a]benzimidazoles and related derivatives." Eur J Med Chem (1995) 30, 327-332.
Ganser-Pronillos et al. "Assembly Properties of the Human Immunodeficiency Virus Type 1 CA Protein." Journal of Virology, Mar. 2004, p. 2545-2552, vol. 78, No. 5.
Gross et al. "In vitro assembly properties of purified bacterially expressed capsid proteins of human immunodeficiency virus." Eur. J. Biochem. 249, 592-600 (1997).
Huseby et al. "Assembly of Human Immunodeficiency Virus Precursor Gag Proteins." The Hournal of Biological Chemistry, vol. 280, No. 18, pp. 17664-17670, May 6, 2005.
Jiang et al. "Enhancement of Human Immunodeficiency Virus Type 1 Infection by Antisera to Peptides from the Envelope Glycoproteins gp120/gp41." J. Exp. Med., vol. 174, Dec. 1991, 1557-1563.
Jiang et al. "N-Substituted Pyrrole Derivatives as Novel Human Immunodeficiency Virus Type 1 Entry Inhibitors that Interfere with the gp41 Six-Helix Bundle Formation and Block Virus Fusion.", Nov. 2004, vol. 48, No. 11, pp. 4349-4359.
Lalezari et al. "Enfuviritude, an HIV-1 Fusion Inhibitor, for Drug-Resistant HIV Infection in North and South America." The New England Hournal of Medicine, May 29, 2003, vol. 348, No. 22.
International Search Report, PCT/US2009/052949 mailed Sep. 4, 2010.

* cited by examiner

*Primary Examiner* — Shengjun Wang
(74) *Attorney, Agent, or Firm* — K&L Gates LLP; Louis C. Cullman; Michelle Glasky Bergman

(57) ABSTRACT

Chemical compounds that disrupt retroviral assembly and maturation are presented herein. More particularly, this disclosure provides small molecule compounds that disrupt the formation and maturation of virus particles and methods of using such small molecules to treat HIV-1 infection.

6 Claims, 3 Drawing Sheets

Control 0.5x

1x

Control 0.5x

1x

3x

Control 0.4 µM

2 µM

10 µM

SMALL MOLECULE INHIBITORS OF RETROVIRAL ASSEMBLY AND MATURATION

CROSS REFERENCE TO RELATED APPLICATIONS

This application claims the benefit under 35 USC §119(e) of U.S. Provisional Patent Application No. 61/087,574 filed on Aug. 8, 2009, the entire contents of which are incorporated by reference herein.

BACKGROUND OF THE INVENTION

Human immunodeficiency virus type 1 (HIV-1) is the etiological agent that causes acquired immunodeficiency syndrome (AIDS). According to the AIDS Epidemic Update (UNAIDS, December 2007) approximately 36 million people are living with HIV-1, particularly in Sub-Saharan Africa and South-East Asia. The introduction of highly active anti-retroviral therapy (HAART) has significantly contributed to the decreased morbidity and mortality among HIV-1 infected people; however, the patient's developed drug resistance severely limits treatment options available. The developed resistance and the failure of several therapies in recent clinical trials have reinforced the critical need to identify and utilize newer targets to develop new classes of anti-HIV-1 drugs that broaden the scope of treatment and reduce development of treatment resistant HIV-1 variants.

HIV-1 infection involves the attachment of the virus to the host cell, reverse transcription of genetic material from viral RNA to DNA, integration of viral DNA with host DNA, replication of viral RNA from DNA, translation of viral RNA to create viral proteins, cleavage of viral proteins, assembly and packaging of viral proteins, and budding from the host cell.

HIV-1 infection of a host immune cell first requires attachment of the virus to the cell membrane. On the surface membrane of all living cells are complex protein structures called "receptors". A receptor is often compared to a lock into which a specific key or "ligand" will fit. Attachment of the virions to receptors on the host membrane enables fusion and the viral contents, including viral RNA, will empty into the cell's cytoplasm. Like other viruses that infect human cells, HIV-1 commandeers the host's machinery to make multiple copies of itself. Once the RNA has been copied and translated into proteins, the viral RNA and associated proteins are packaged and released from the host cell, taking with them a piece of the cell membrane.

There are only nine genes in the HIV-1 genome. These genes have the code necessary to produce structural proteins, such as the viral core and enzymes like reverse transcriptase, integrase, and protease. One of the most important genes, the gag gene, encodes the Gag protein, the critical structure protein of HIV-1. In human cells infected by HIV-1, the viral Gag protein directs assembly of nascent viral particles at the plasma membrane, and thus, is a good target for disruption of retroviral assembly.

SUMMARY OF THE INVENTION

The present disclosure describes pharmaceutical compositions comprising a therapeutically effective amount of a compound of formula I or a pharmaceutically acceptable salt or ester thereof;

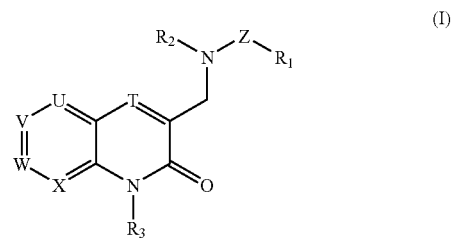

(I)

wherein $R_1$ and $R_2$ are independently a moiety selected from the group consisting of $(C_{1-6})$alkyl, substituted or unsubstituted $(C_{1-6})$alkyl, substituted or unsubstituted $(C_{1-6})$alkoxy, substituted or unsubstituted phenyl, substituted or unsubstituted benzyl, substituted or unsubstituted benzyloxy, substituted or unsubstituted alkyl phenyl, substituted or unsubstituted aminophenyl, cycloalkyl, substituted or unsubstituted aryl, substituted or unsubstituted heterocycle, and substituted or unsubstituted alkyl heterocycle; $R_3$ is a moiety selected from the group consisting of H, and substituted or unsubstituted $(C_{1-6})$alkyl; Z is C=O, C=S or S(=O)=O; and T, U, V, W and X are independently selected from $CR_4$ or N, wherein $R_4$ is a moiety selected from the group consisting of hydrogen, substituted or unsubstituted $(C_{1-6})$alkyl, substituted or unsubstituted $(C_{1-6})$alkoxy, hydroxyl alkyl, halogen, nitrile, amino, nitro, carboxyl, alkyl amino sulphonyl, substituted or unsubstituted aryl amino sulphonyl, substituted or unsubstituted phenyl, and substituted or unsubstituted benzyl. In some embodiments, the compound is selected from the group of compounds in Table 1. In other embodiments, the composition includes at least two compounds from Table 1.

The present disclosure also describes pharmaceutical compositions comprising a therapeutically effective amount of a compound of formula II or a pharmaceutically acceptable salt or ester thereof;

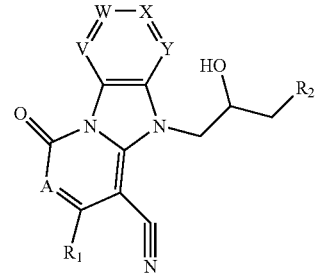

(II)

wherein $R_1$ is a moiety selected from the group consisting of hydrogen, substituted or unsubstituted $(C_{1-6})$alkyl, substituted or unsubstituted $(C_{1-6})$alkoxy, hydroxyl, hydroxy alkyl, halogen, nitrile, nitro, amino, sulphonyl, sulphonamido; $R_2$ is a moiety selected from the group consisting of substituted or unsubstituted $(C_{1-6})$alkyl, substituted or unsubstituted $(C_{1-6})$ alkoxy, carboxyl, alkyl amino sulphonyl, substituted or unsubstituted aryl amino sulphonyl, substituted or unsubstituted phenyl, substituted or unsubstituted benzyl, substituted or unsubstituted benzyloxy, substituted or unsubstituted alkyl phenyl, substituted or unsubstituted aminophenyl, cycloalkyl, substituted or unsubstituted aryl, substituted or unsubstituted heterocycle, and substituted or unsubstituted alkyl heterocycle; and A, V, W, X and Y are independently selected from $CR_3$ or N, wherein $R_3$ is a moiety selected from the group consisting of hydrogen, $(C_{1-6})$alkyl, substituted or unsubstituted ($C_{1-6}$)alkyl, substituted or unsubstituted ($C_{1-6}$) alkoxy, hydroxyl, hydroxy alkyl, halogen, nitrile, amino, nitro. In some embodiments, the compound is selected from the group of compounds in Table 2. In other embodiments, the composition includes at least two compounds selected from Tables 1 and 2.

The present compositions may also include one or more pharmaceutically acceptable excipients and/or one or more additional therapeutic agents.

The present systems and methods are also directed towards methods for disrupting HIV-1 assembly and replication. The methods may include administering to cells a pharmaceutical composition comprising a pharmaceutically effective amount of a compound of formula I or formula II, or pharmaceutically acceptable salts or esters thereof. The methods may utilize any of the compositions disclosed herein, including those disclosed in Tables 1 and 2.

The methods may further include administering a compound of formula I and/or formula II with at least one additional therapeutic agent selected from the group consisting of reverse transcriptase inhibitors, protease inhibitors, fusion inhibitors, integrase inhibitors, chemokine receptor (CXCR4, CCR5) inhibitors, interleukin-2, hydroxyurea, monoclonal antibodies, cytokines, and combinations thereof.

DEFINITION OF TERMS

Figure 1A:
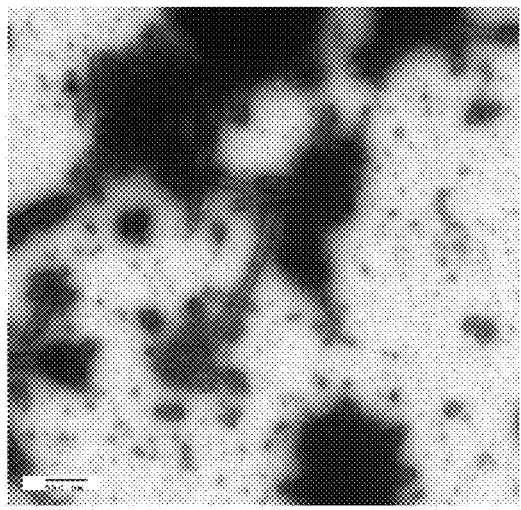
FIG. 1 illustrates negatively stained electron microscopy (EM) images of mature virus-like particles resulting from in vitro assembly of the capsid protein (CA) of HIV-1 in the absence (control) and presence of NYAD-S6 (FIGS. 1A-C) or NYAD-S8 (FIGS. 1D-G).

The following definition of terms is provided as a helpful reference for the reader. The terms used herein have specific meanings as they are related to the present disclosure. Every effort has been made to use terms according to their ordinary and common meaning. However, where a discrepancy exists between the common ordinary meaning and the following definitions, these definitions supercede common usage.

The term "alicyclic," as used herein, refers to compounds which combine the properties of aliphatic and cyclic compounds and include, but are not limited to, cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH2-cyclopropyl, cyclobutyl, —CH2-cyclobutyl, cyclopentyl, —CH2-cyclopentyl-n, cyclohexyl, —CH2-cyclohexyl, cyclohexenylethyl, cyclohexanylethyl, norborbyl moieties and the like, which may bear one or more substituents.

The term "aliphatic," as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms; in some embodiments, the term may refer to group having about 1-3 carbon atoms. In certain embodiments, alkyl, alkenyl and alkynyl groups employed contain about 1-20 aliphatic carbon atoms. In certain other embodiments, alkyl, alkenyl, and alkynyl groups employed contain about 1-10 aliphatic carbon atoms. In yet other embodiments, alkyl, alkenyl, and alkynyl groups employed contain about 1-8 aliphatic carbon atoms. In still other embodiments, alkyl, alkenyl, and alkynyl groups employed contain about 1-6 aliphatic carbon atoms. In yet other embodiments, alkyl, alkenyl, and alkynyl groups employed contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl moieties and the like, which may bear one or more substituents. Illustrative alkenyl groups include, but are not limited to, for example, ethenyl, propenyl, butenyl, 1-methyl-2-buten-1-yl and the like. Representative alkynyl groups include, but are not limited to, ethynyl, 2-propynyl (propargyl), 1-pro[rho]ynyl and the like.

The terms "alkoxy" or "alkyloxy," as used herein, refers to an alkyl group, as previously defined, attached to the parent molecular moiety through an oxygen atom. In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups include, but are not limited to, melhoxy, ethoxy, propoxy, isopropoxy, n-butoxy, tert-butoxy, neopentoxy and n-hexoxy.

In general, the term "aromatic moiety," as used herein, refers to stable substituted or unsubstituted, unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl. It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic) heteroaromatic, -(heteroaliphatic)heteroaromatic, -(alkyl)aromatic, -(heteroalkyl) aromatic, -(alkyl)heteroaromatic, and -(heteroalkyl)heteroaromatic moieties. Thus, as used herein, "aromatic or heteroaromatic moieties" is interchangeable with aromatic, heteroaromatic, -(alkyl)aromatic, -(heteroalkyl)aromatic, -(heteroalkyl)heteroaromatic, and -(heteroalkyl)heteroaromatic. Substituents include, but are not limited to, any of the substituents described herein resulting in the formation of a stable compound.

The term "aryl" refers to aromatic moieties, as described above, excluding those attached via an aliphatic (e.g., alkyl) or heteroaliphatic (e.g., heteroalkyl) moiety. In certain embodiments, "aryl" refers to mono- or bicyclic carbocyclic ring systems having one or two rings satisfying the Huckel rule for aromaticity, including, but not limited to, phenyl, naphthyl, tetrahydronaphthyl, indanyl, indenyl and the like. Substituents for aryl and heteroaryl moieties include, but are not limited to, any of the previously mentioned substituents, i.e., the substituents recited for aliphatic moieties or for other moieties as disclosed herein, resulting in the formation of a stable compound.

The term "cycloalkyl," as used herein, refers to cyclic alkyl groups having three to seven carbon atoms. Suitable cycloalkyls include, but are not limited to, cyclopropyl, cyclobutyl, cyclopentyl, cyclohexyl, cycloheptyl, and the like, which, as in the case of aliphatic, heteroaliphatic or heterocyclic moieties, may optionally be substituted. An analogous convention applies to other generic terms such as "cycloalkenyl," "cycloalkynyl" and the like.

As used herein, an "ester," may be derived from a carboxylic acid group located on any portion of the compounds described herein. While not intending to be limiting, an ester may be an alkyl ester, an aryl ester, or a heteroaryl ester.

The terms "halo" and "halogen," as used herein, refer to an atom selected from fluorine, chlorine, bromine and iodine.

The term "haloalkyl" denotes an alkyl group having one, two, or three halogen atoms attached thereto and is exemplified by, but not limited to, such groups as chloromethyl, bromoethyl, and trifluoromethyl.

The term "halogenated" denotes a moiety having one, two or three halogen atoms attached thereto.

The terms "heteroalicyclic," "heterocycloalkyl" or "heterocyclic," as used herein, refer to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic five-, six- or seven-membered ring or a polycyclic group, including, but not limited to a bi- or tri-cyclic group comprising fused six-membered rings having between one and three heteroatoms independently selected from oxygen, sulfur and nitrogen, wherein: (i) each five-membered ring has zero to two double bonds and each six-membered ring has zero to two double bonds; (ii) the nitrogen and sulfur heteroatoms may optionally be oxidized; (iii) the nitrogen heteroatom may optionally be quaternized; and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. Additionally, it will be appreciated that in some embodiments, any of the alicyclic or heteroalicyclic moieties described above and herein may comprise an aryl or heteroaryl moiety fused thereto. Additional examples of generally applicable substituents are illustrated by the specific embodiments shown in the Tables and Examples described herein.

The term "heteroaliphatic," as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, i.e., in place of carbon atoms. Thus, a 1-6 atom heteroaliphatic linker having at least one nitrogen atom in the heteroaliphatic main chain, as used herein, refers to a carbon aliphatic chain wherein at least one carbon atom is replaced with a nitrogen atom, and wherein any one or more of the remaining five carbon atoms may be replaced by an oxygen, sulfur, nitrogen, phosphorus or silicon atom. As used herein, a one-atom heteroaliphatic linker having at least one nitrogen atom in the heteroaliphatic main chain refers to —NH— or —NR— where R is aliphatic, heteroaliphatic, acyl, aromatic, heteroaromatic or a nitrogen protecting group. Heteroaliphatic moieties may be branched or linear unbranched. In some embodiments, heteroaliphatic moieties are substituted by independent replacement of one or more of the hydrogen atoms thereon with one or more moieties including, any of the substituents described above.

The term "heteroaromatic moiety," as used herein, refers to stable substituted or unsubstituted, unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl. It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, "aromatic or heteroaromatic moieties" is interchangeable with aromatic, heteroaromatic, -(alkyl)aromatic, -(heteroalkyl)aromatic, -(heteroalkyl)heteroaromatic and -(heteroalkyl) heteroaromatic. Substituents include, but are not limited to, any of the previously mentioned substituents resulting in the formation of a stable compound.

The term "heteroaryl," as used herein, refers to heteroaromatic moieties, as described above, excluding those attached via an aliphatic (e.g., alkyl) or heteroaliphatic (e.g., heteroalkyl) moiety. In certain embodiments of the present disclosure, the term "heteroaryl" refers to a cyclic unsaturated radical having from about five to about ten ring atoms of which one ring atom is selected from sulfur, oxygen and nitrogen; zero, one or two ring atoms are additional heteroatoms independently selected from sulfur, oxygen and nitrogen; and the remaining ring atoms are carbon, the radical being joined to the rest of the molecule via any ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl and the like. Substituents for aryl and heteroaryl moieties include, but are not limited to, any of the previously mentioned substituents, i.e., the substituents recited for aliphatic moieties or for other moieties, as disclosed herein, resulting in the formation of a stable compound.

The term "HIV capsid" or "capsid" refers to an ordered icosahedral particle composed of approximately 1500 Gag polypeptides within which is normally housed HIV-1 specific genomic material and enzymes. The capsid is first formed as an immature structure, and later undergoes a "maturation" event mediated by a HIV-specific protease. The HIV-specific protease cleaves Gag polypeptides that form the immature capsid into smaller proteins. This results in a change in the shape of the capsid to the mature, cone shaped capsid.

As used herein, the term "inhibit," "inhibition," "inhibitory" and "inhibitory activity" refers to slowing, decreasing, interrupting, arresting or suppressing HIV assembly, maturation and replication activity so as to enable prolonging the survivability of the patient. In some embodiments, the claimed composition may suppress 90%, 80%, 70%, 60%, 50%, 40%, 30%, 20%, or 10% of the retroviral activity. $IC_{50}$ is well understood by a person of skill in the art to be the accepted measure of the effectiveness of inhibition. The measurement indicates how much of a particular substance is necessary to decrease or inhibit a particular activity by 50%.

A "pharmaceutically acceptable derivative," as used herein, denotes any pharmaceutically acceptable salt, ester, or salt of such ester of a disclosed compound, or any other adduct or derivative which, upon administration to a patient, provides (directly or indirectly) a compound as otherwise described herein, or a metabolite or residue thereof. Pharmaceutically acceptable derivatives include, among others, prodrugs.

As used herein, the term "pharmaceutically acceptable salt" or "salt" refers to those salts which are, as appreciated by one of ordinary skill in the art, suitable for use in contact with the tissues of humans and other animals without undue toxicity, irritation, allergic response and the like, and are commensurate with a reasonable benefit/risk ratio. Many pharmaceutically acceptable salts are well known in the art. For example, S. M. Berge et al. describe pharmaceutically acceptable salts in detail in J. Pharmaceutical Sciences 66:1-19, 1977, incorporated herein in its entirety by reference. Pharmaceutically acceptable salts of compounds disclosed herein include those derived from suitable inorganic and organic acids and bases. Examples of pharmaceutically acceptable salts include, but are not limited to, hydrochloride, hydrobromide, hydroiodide, sulfate, phosphate, acetate, propionate, lactate, maleate, malate, succinate, tartrate salts, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts and the like. Salts derived from appropriate bases include alkali metal, alkaline earth salts. The present disclosure also envisions the quaternization of any basic nitrogen-containing groups of compounds disclosed herein. Water or oil-soluble or dispersable products may be obtained by such quaternization. Representative alkali or alkaline earth metal salts include sodium, lithium, potassium, calcium, magnesium and the like. Further, pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein "prodrug" refers to a compound which is converted to a therapeutically active compound after administration, and the term should be interpreted as broadly herein as is generally understood in the art. While not intending to limit the scope of the present description, conversion may occur by hydrolysis of an ester group or some other biologically labile group. Generally, but not necessarily, a prodrug is inactive or less active than the therapeutically active compound to which it is converted. Ester prodrugs of the compounds disclosed herein are contemplated.

Generally, a "small molecule" is understood by a skilled artisan to be an organic molecule that is less than about 5 kilodaltons (kD) in size. In some embodiments, the small molecule is less than about 3 kD, 2 kD, or 1 kD. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

As used herein, the term "stable" refers to compounds which possess stability or permanence sufficient to maintain the integrity of the compound for a sufficient period of time to be detected and preferably for a sufficient period of time to be useful for purposes detailed herein.

Compounds, as described herein, may be "substituted" with any number of substituents or functional moieties. In general, the term "substituted," whether preceded by the term "optionally" or not, refers to replacement of hydrogen radicals in a given structure with the radical of a specified substituent. The term "unsubstituted" refers to structures where hydrogen is still present and has not been substituted. More than one position in any given structure may be substituted with more than one substituent selected from a specified group; the substituent may be either the same or different at every position. As used herein, the term "substituted" is contemplated to include all permissible substituents of organic compounds. In a broad aspect, permissible substituents include, but are not limited to, acyclic and cyclic, branched and unbranched, carbocyclic, heterocyclic, aromatic and non-aromatic, carbon and heteroatom substituents of organic compounds.

For purposes of this disclosure, heteroatoms such as nitrogen may have hydrogen substituents and/or any permissible substituents of organic compounds described herein which satisfy valencies of the heteroatoms. Furthermore, this disclosure is not intended to be limited in any manner by the permissible substituents of organic compounds. Combinations of substituents and variables envisioned by the present disclosure are preferably those that result in the formation of stable compounds useful for purposes described herein. Examples of substituents include, but are not limited to, aliphatic; heteroaliphatic; alicyclic; heteroalicyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$), —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by specific embodiments described herein.

The term "therapeutically effective amount" or "pharmaceutically effective amount" means an amount of composition sufficient to, when administered to a subject suffering from or susceptible to HIV infection and/or one or more associated diseases, disorders or conditions, treat HIV infection and/or associated disease(s), disorder(s) or condition(s).

The term "thioalkyl," as used herein, refers to an alkyl group, as previously defined, attached to the parent molecular moiety through a sulfur atom. In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of thioalkyl groups include, but are not limited to, methylthio, ethylthio, propylthio, isopropylthio, and n-butylthio.

The terms "treat," "treatment" or "treating," as used herein, refer to partially or completely alleviating, inhibiting, preventing, curing, delaying the onset of, reducing incidence of, ameliorating and/or relieving one or more symptoms or features of a particular disease, disorder or condition (e.g., HIV infection).

It will be appreciated that, as used herein, terms such as, but not limited to, "aliphatic," "heteroaliphatic," "alkyl," "alkenyl," "alkynyl," "heteroalkyl," "heteroalkenyl" and "heteroalkynyl" encompass substituted and unsubstituted, saturated and unsaturated, and linear and branched groups. Similarly, terms such as, but not limited to, "alicyclic," "heterocyclic," "heterocycloalkyl" and "heterocycle" encompass substituted and unsubstituted, and saturated and unsaturated groups. Additionally, terms such as, but not limited to, "cycloalkyl," "cycloalkenyl," "cycloalkynyl," "heterocycloalkyl," "heterocycloalkenyl," "heterocycloalkynyl," "aromatic," "heteroaromatic," "aryl" and "heteroaryl," used alone or as part of a larger moiety, encompass both substituted and unsubstituted groups.

DETAILED DESCRIPTION OF THE INVENTION

Gag polyproteins are necessary for the assembly and budding of infectious human immunodeficiency virus 1 (HIV-1). Assembly of HIV-1 is generally thought to occur through the controlled polymerization of Gag polyproteins, which are transported to a plasma membrane, where assembly takes place. Virus particles then form and bud out as spherical immature non-infectious particles. Immediately after budding, the particles undergo a process known as maturation. During this maturation step the Gag proteins are sequentially cleaved by viral proteases, triggering a dramatic change in particle morphology and an electron-dense core is formed surrounded by a conical capsid. The Gag proteins are sequentially cleaved by viral proteases to matrix (MA), capsid (CA), nucleocapsid (NC), p6 domains, and two spacer proteins, P1 and P2.

A capsid protein is a Gag cleavage product and it plays a central role in forming the conical core of the virus that surrounds the viral genome. The capsid is composed of many subunits which form several homo- or hetero-polymer proteins. Extended polypeptide chains from one subunit may extend to domains of a neighboring subunit, helping stabilize the capsid through salt bridges, hydrogen bonds and hydrophobic interactions. Mature capsid formation is important to viral assembly and maturation, and thus, disruption of capsid functioning is a potential target for developing new generation HIV-1 therapies. The major capsid protein p24 (also called CA) is a hydrophobic protein consisting of an N-terminal domain (NTD) and a C-terminal domain (CTD).

Several peptide and small molecules that disrupt HIV-1 assembly include small molecule inhibitors CAP-1, CAP-2, PA-457 and capsid assembly inhibitor (CAI). These compounds affect virus stability and/or assembly. CAP-1 showed dose-dependent HIV-1 inhibition in viral infectivity assays but low binding affinity ($K_d$~800 µM). CAP-2 was cytotoxic. PA-457 has shown low nM antiviral potency in cell culture, and CAI successfully disrupted HIV-1 assembly in vitro but lacks cell permeability, and therefore, is not a viable drug candidate.

The formation of a mature capsid is critical in viral infectivity, playing a crucial role in viral assembly, maturation and early post-entry steps. Mutations in either the NTD or CTD may lead to defects in viral assembly and release and ultimately, inhibit viral infectivity. The NTD binds cyclophylin A and is important for viral core formation. The CTD contains critical determinants of Gag oligomerization, essential for viral assembly. The CTD also encompasses the most conserved segment of Gag known as the major homology region (MHR). Isolated capsid CTD forms a dimer in solution, which has been shown to be a major driving force in Gag assembly and maturation. Mutation of the dimer interface residues in the CTD monomer disrupts dimer formation, impairs capsid assembly and renders a virus noninfectious. Thus, the capsid CTD plays an important role in viral assembly and maturation and capsid disruption is a particularly promising avenue for new generation anti-HIV-1 drugs.

The x-ray structure of CAI (a known peptide inhibitor that lacks cell permeability, as discussed above) in complex with capsid CTD revealed molecular details of the peptide-based inhibitor's structural binding the hydrophobic pocket and the surrounding area. CAI forms an α-helical conformation and binds to a hydrophobic pocket with a $K_d$~15 µM.

Virtual screening based on high-throughput flexible docking is an emerging technology for structure-based rational lead discovery. Rapid accumulation of high-resolution improvements in docking and scoring technology makes virtual screening an attractive alternative to traditional methods of lead discovery. Docking-based virtual screening techniques have become a central feature of many drug discovery efforts because of their ability to sample a virtually infinite variety of drug-like molecules without synthesizing and experimentally testing every screened molecule.

The ZINC 7 database (Irwin and Shoichet, *J. Chem. Inf. Model.* 2005; 45(1):177-82) was selected for docking-based virtual screening study. The database contains ~4.6 million pre-filtered compounds in a ready-to-dock stage in three-dimensional (3D) format. The automated docking software GLIDE 8.0 (Schrödinger, Portland, Oreg.) was used in conjunction with the ZINC database. GLIDE 8.0 applies a two-stage scoring process to sort the best conformations and orientations of the ligand based on its interaction pattern with the receptor.

Approximately 40,000 drug-like molecules from the ZINC database were screened and the 200 top-scored docking compounds were selected for 3D analysis to identify compounds having the best possible interactions with the CTD. Based on the 3D analysis, certain compounds were selected for experimentation. Based on the potency and selectivity of the tested compounds, additional analogs were tested to determine antiviral activity against HIV-1.

The present disclosure relates to the discovery of particular small molecules that interfere with HIV-1 assembly, maturation and budding. The small molecule of formulas I and II and their pharmaceutically acceptable salts and esters may be used as inhibitors of HIV-1 capsid assembly in cell culture. Particularly, this new class of anti-HIV-1 compounds target the CTD (amino acids 146-231) of the HIV-1 capsid. The molecules and mechanisms of action are novel and distinct from those currently known to persons having ordinary skill in the art.

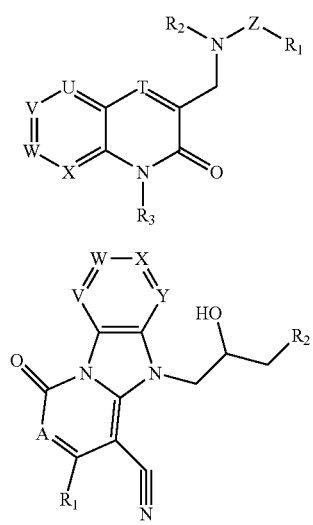

The various substituents and variables for the compounds of formula I are defined as follows:

$R_1$ and $R_2$ are independent a moiety selected from the group consisting of $(C_{1-6})$alkyl, substituted or unsubstituted $(C_{1-6})$alkyl, substituted or unsubstituted $(C_{1-6})$alkoxy, substituted or unsubstituted phenyl, substituted or unsubstituted benzyl, substituted or unsubstituted benzyloxy, substituted or unsubstituted alkyl phenyl, substituted or unsubstituted aminophenyl, cycloalkyl, substituted or unsubstituted aryl, substituted or unsubstituted heterocycle, and substituted or unsubstituted alkyl heterocycle.

$R_3$ is a moiety selected from the group consisting of H, and substituted or unsubstituted $(C_{1-6})$alkyl.

Z is C=O, C=S or S(=O)=O.

T, U, V, W and X are independently selected from $CR_4$ or N, wherein $R_4$ is a moiety selected from the group consisting of hydrogen, substituted or unsubstituted $(C_{1-6})$alkyl, substituted or unsubstituted $(C_{1-6})$alkoxy, hydroxyl alkyl, halogen, nitrile, amino, nitro, carboxyl, alkyl amino sulphonyl, substituted or unsubstituted aryl amino sulphonyl, substituted or unsubstituted phenyl, and substituted or unsubstituted benzyl.

Table 1 exemplifies some embodiments of formula I and includes the compound's corresponding $IC_{50}$ (concentration of a compound that provides 50% inhibition of HIV-1 p24) and $CC_{50}$ (concentration of a compound that causes 50% cytotoxicity) data. Compounds of formula I are not limited to those illustrated in Table 1.

TABLE 1

| Chemical Compound | Structure | $IC_{50}$ ($\mu M$)[1] | $CC_{50}$ ($\mu M$)[2] |
|---|---|---|---|
| NYAD-S2 | 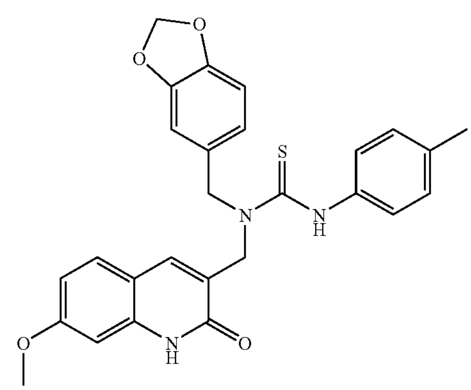 | B | D |
| NYAD-S3 | 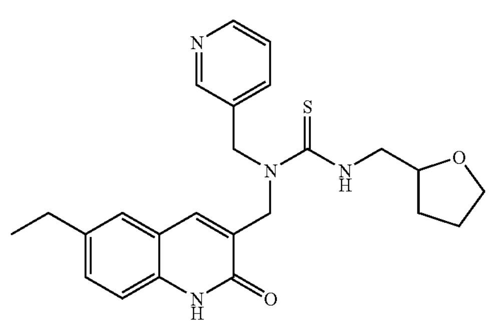 | B | D |

TABLE 1-continued

| Chemical Compound | Structure | IC$_{50}$ (µM)[1] | CC$_{50}$ (µM)[2] |
|---|---|---|---|
| NYAD-S4 | 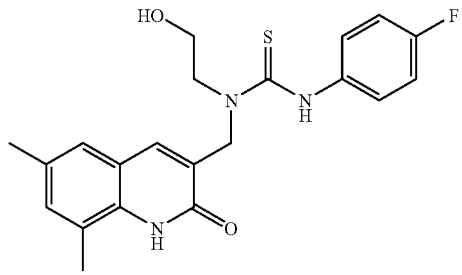 | B | D |
| NYAD-S5 | 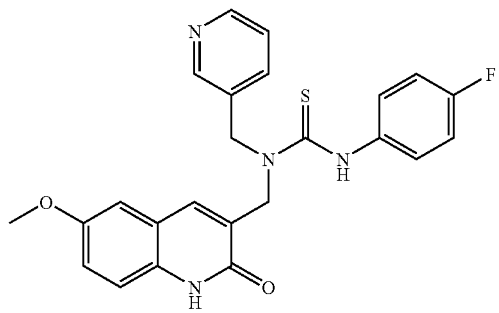 | B | D |
| NYAD-S6 | 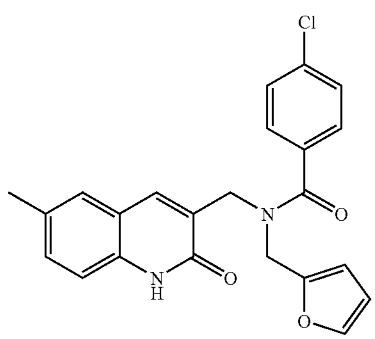 | A | D |
| NYAD-S20 | 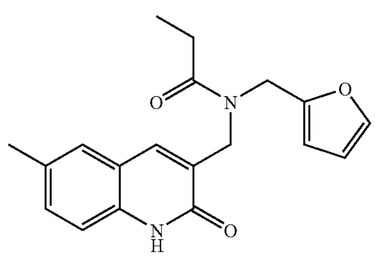 | B | D |
| NYAD-S21 | 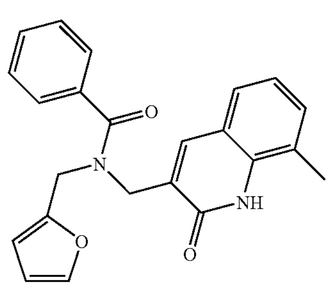 | A | D |

TABLE 1-continued

| Chemical Compound | Structure | IC$_{50}$ (μM)[1] | CC$_{50}$ (μM)[2] |
|---|---|---|---|
| NYAD-S22 | 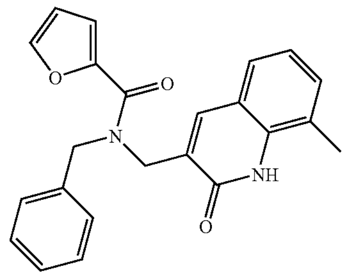 | B | D |
| NYAD-S23 | 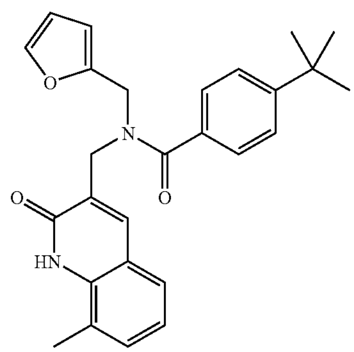 | B | D |
| NYAD-S24 | 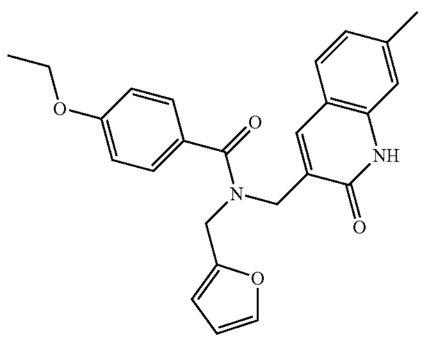 | B | D |
| NYAD-S25 | 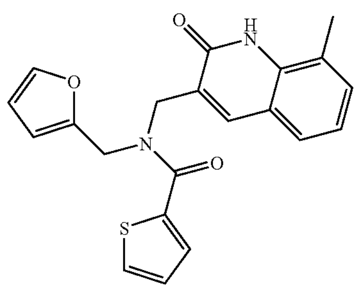 | B | D |
| NYAD-S26 | 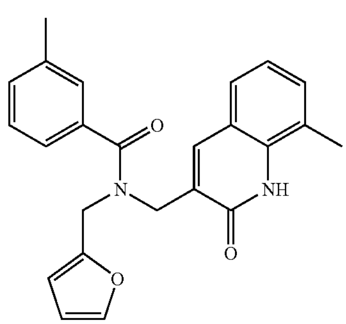 | B | D |

TABLE 1-continued

| Chemical Compound | Structure | IC$_{50}$ (µM)[1] | CC$_{50}$ (µM)[2] |
|---|---|---|---|
| NYAD-S27 | 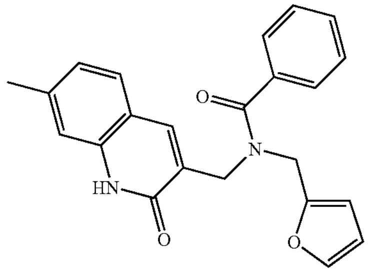 | B | D |
| NYAD-S28 | 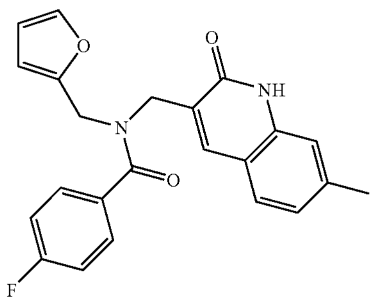 | B | D |
| NYAD-S29 | 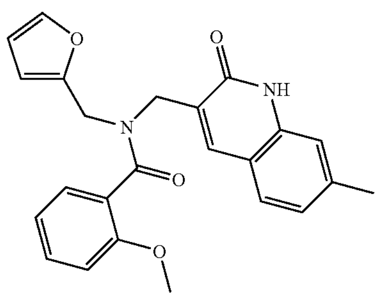 | B | D |
| NYAD-S30 | 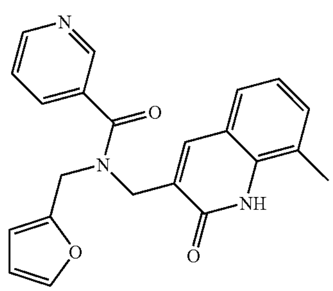 | B | D |
| NYAD-S31 | 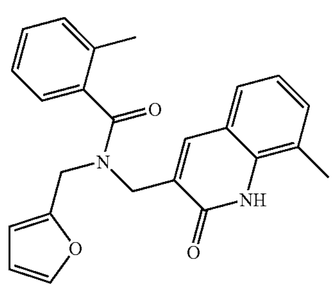 | B | D |

TABLE 1-continued
| Chemical Compound | Structure | IC$_{50}$ (μM)[1] | CC$_{50}$ (μM)[2] |
|---|---|---|---|
| NYAD-S32 | 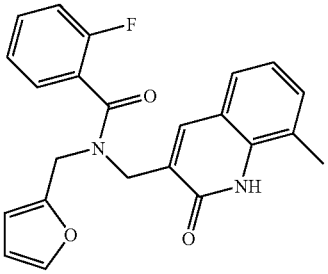 | B | D |
| NYAD-S33 | 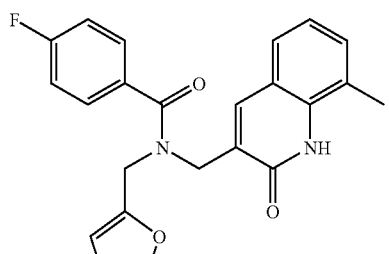 | B | D |
| NYAD-S34 | 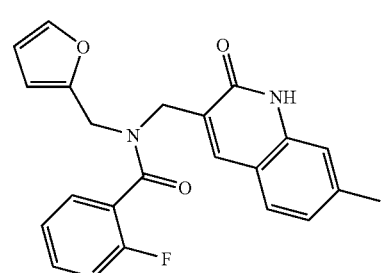 | B | D |
| NYAD-S35 | 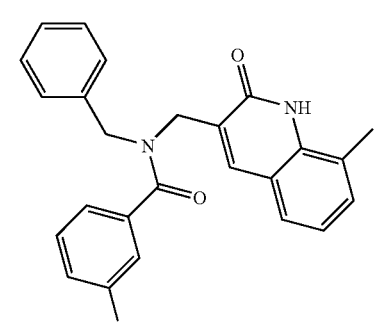 | B | D |
| NYAD-S36 | 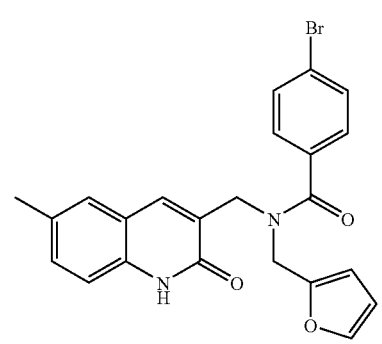 | A | D |

TABLE 1-continued
| Chemical Compound | Structure | IC$_{50}$ (µM)[1] | CC$_{50}$ (µM)[2] |
|---|---|---|---|
| NYAD-S37 | 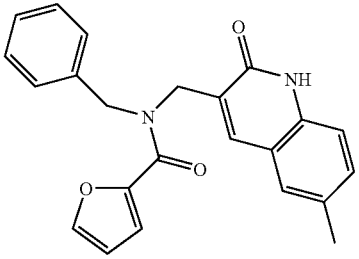 | A | D |
| NYAD-S38 | 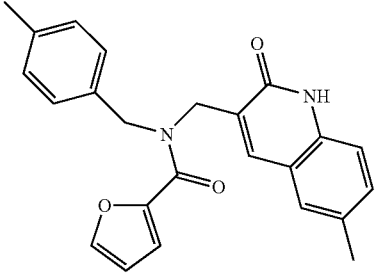 | A | D |
| NYAD-S39 | 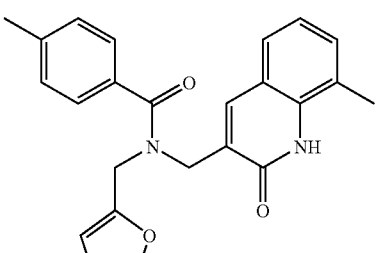 | B | D |
| NYAD-S40 | 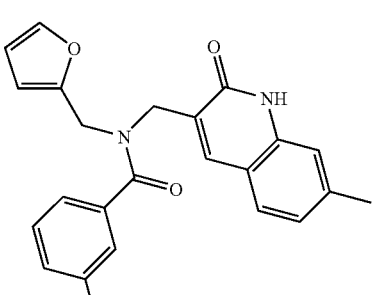 | B | D |
| NYAD-S41 | 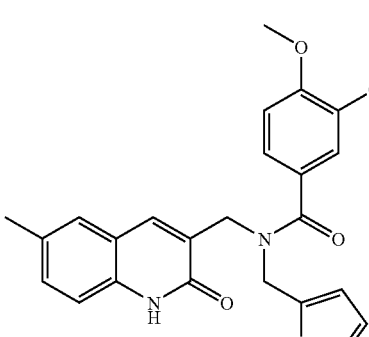 | B | D |

TABLE 1-continued

| Chemical Compound | Structure | IC$_{50}$ (μM)[1] | CC$_{50}$ (μM)[2] |
| --- | --- | --- | --- |
| NYAD-S42 | 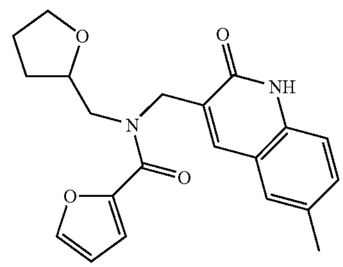 | B | D |
| NYAD-S43 | 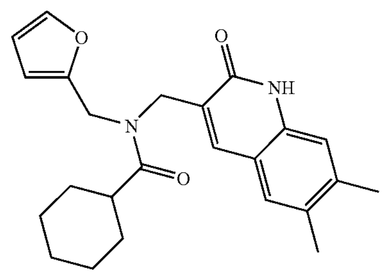 | B | D |
| NYAD-S44 | 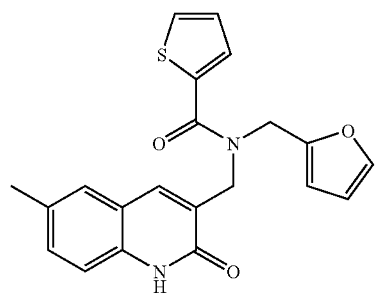 | B | D |
| NYAD-S45 | 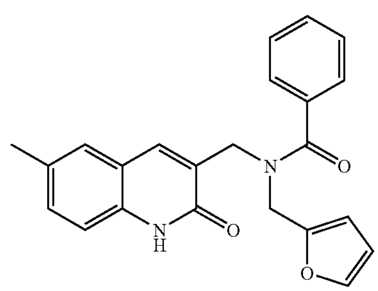 | A | D |
| NYAD-S46 | 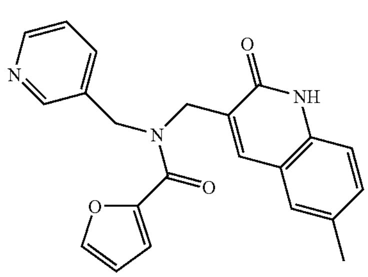 | B | D |

TABLE 1-continued

| Chemical Compound | Structure | IC$_{50}$ (μM)[1] | CC$_{50}$ (μM)[2] |
|---|---|---|---|
| NYAD-S47 | 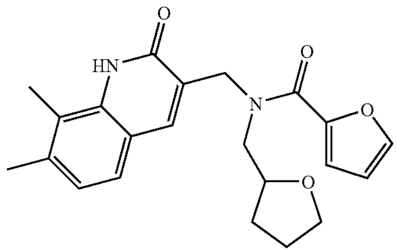 | B | D |
| NYAD-S48 | 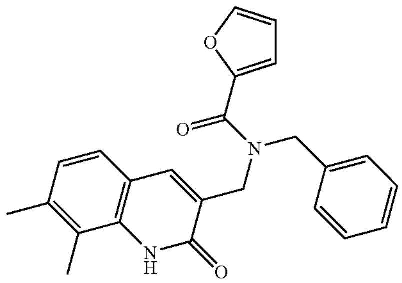 | B | D |
| NYAD-S49 | 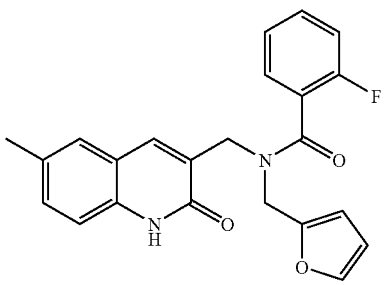 | B | D |
| NYAD-S50 | 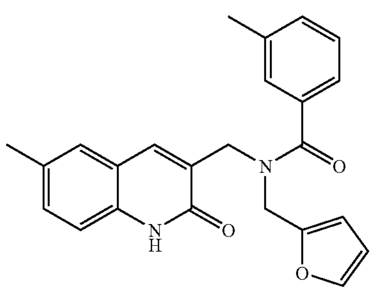 | B | D |
| NYAD-S51 | 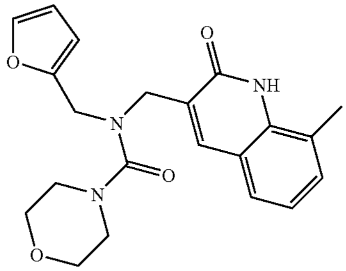 | B | D |

TABLE 1-continued

| Chemical Compound | Structure | IC$_{50}$ (μM)[1] | CC$_{50}$ (μM)[2] |
|---|---|---|---|
| NYAD-S61 | 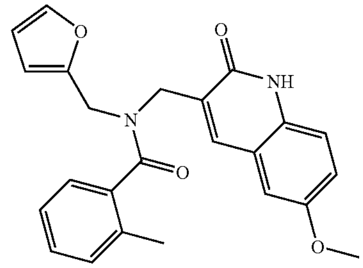 | B | D |
| NYAD-S80 | 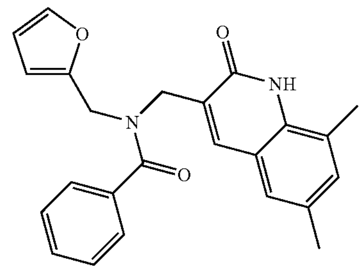 | B | D |
| NYAD-S81 | 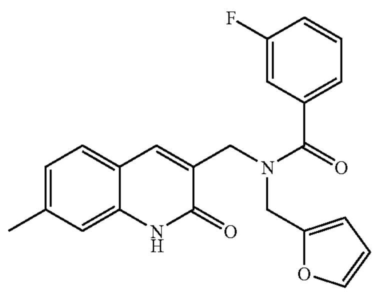 | A | D |
| NYAD-S82 | 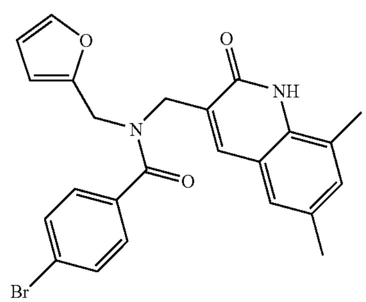 | B | D |
| NYAD-S84 | 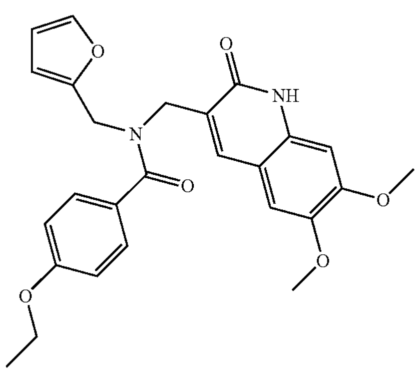 | B | D |

TABLE 1-continued
| Chemical Compound | Structure | IC$_{50}$ (µM)[1] | CC$_{50}$ (µM)[2] |
|---|---|---|---|
| NYAD-S85 | 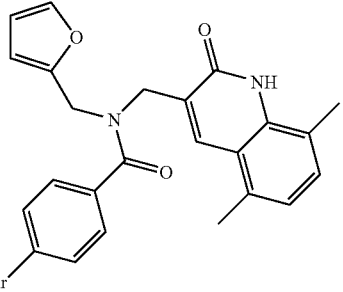 | B | D |
| NYAD-S89 | 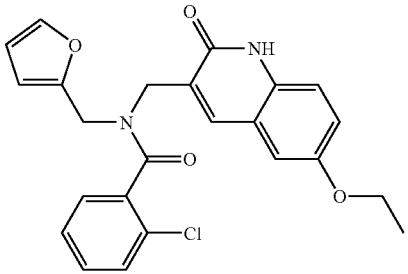 | B | D |
| NYAD-S90 | 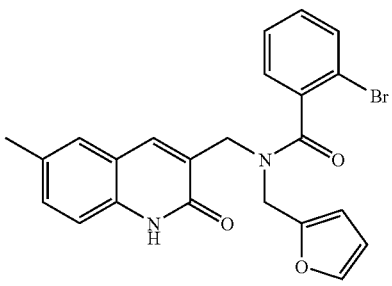 | B | D |
| NYAD-S91 | 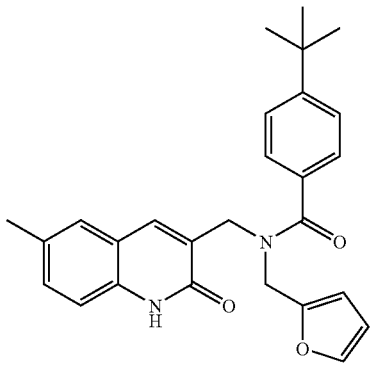 | B | D |
| NYAD-S92 | 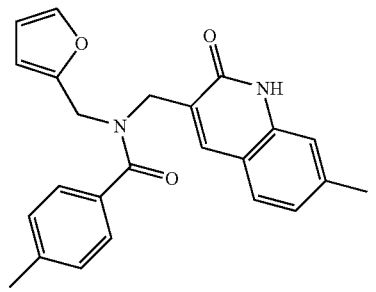 | B | D |

TABLE 1-continued

| Chemical Compound | Structure | IC$_{50}$ (μM)[1] | CC$_{50}$ (μM)[2] |
|---|---|---|---|
| NYAD-S94 | 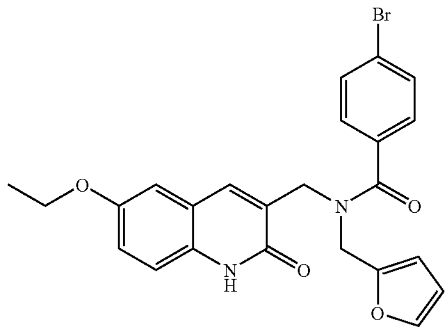 | B | D |
| NYAD-S95 | 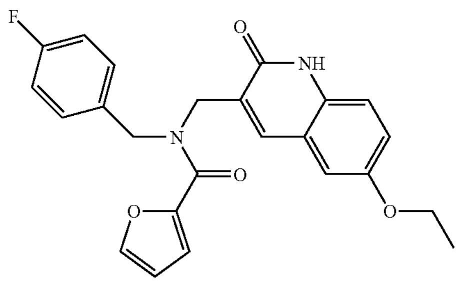 | B | D |
| NYAD-S96 | 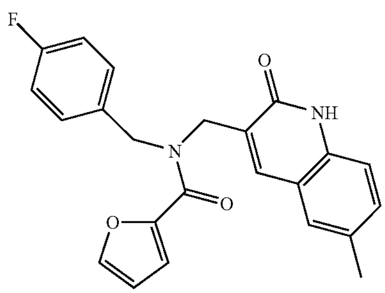 | B | D |
| NYAD-S97 | 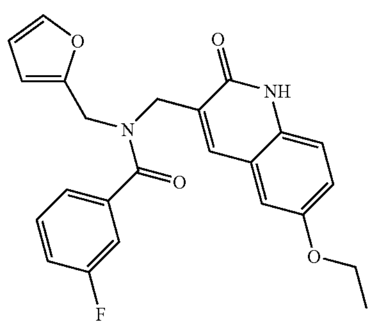 | B | C |
| NYAD-S98 | 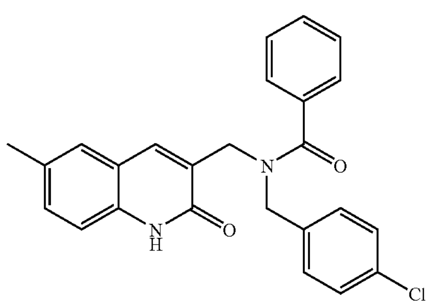 | B | D |

TABLE 1-continued
| Chemical Compound | Structure | IC$_{50}$ (μM)[1] | CC$_{50}$ (μM)[2] |
|---|---|---|---|
| NYAD-S99 | 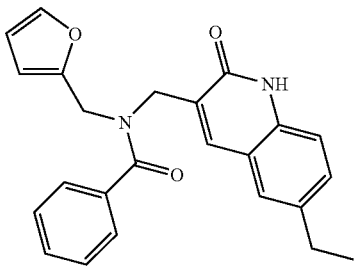 | B | D |
| NYAD-S100 | 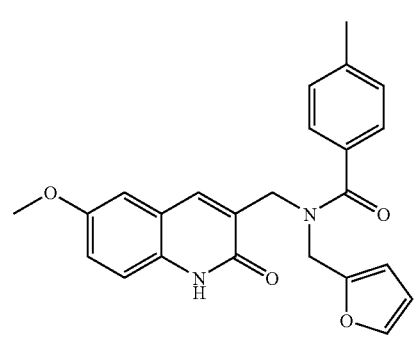 | A | D |
| NYAD-S101 | 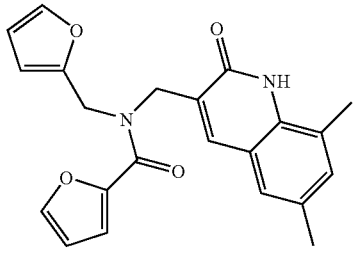 | B | D |
| NYAD-S102 | 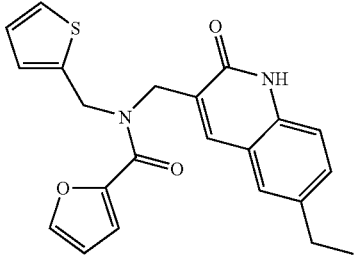 | B | D |
| NYAD-S103 | 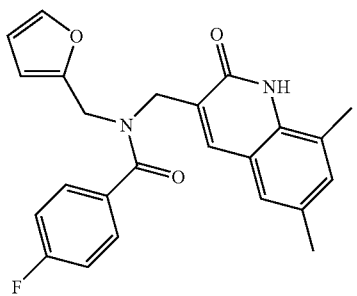 | B | D |

TABLE 1-continued

| Chemical Compound | Structure | IC$_{50}$ (μM)[1] | CC$_{50}$ (μM)[2] |
|---|---|---|---|
| NYAD-S104 | 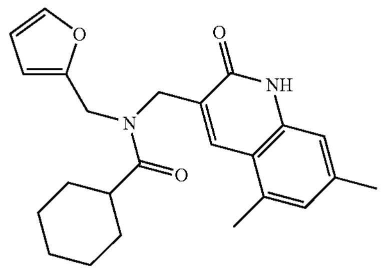 | B | D |
| NYAD-S105 | 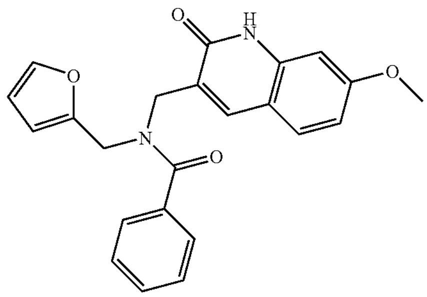 | B | D |
| NYAD-S106 | 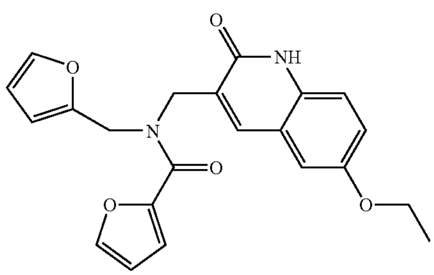 | B | D |
| NYAD-S107 | 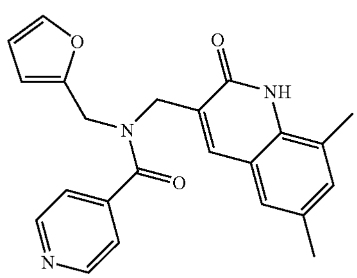 | B | D |
| NYAD-S108 | 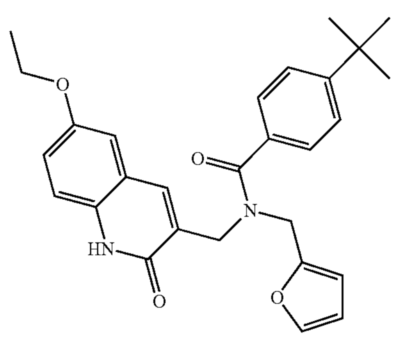 | B | D |

TABLE 1-continued
| Chemical Compound | Structure | IC$_{50}$ (μM)[1] | CC$_{50}$ (μM)[2] |
|---|---|---|---|
| NYAD-S109 | 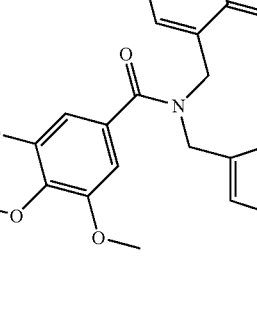 | B | D |
| NYAD-S110 | 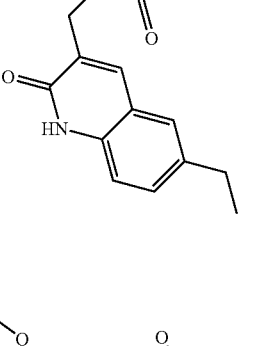 | B | D |
| NYAD-S111 | 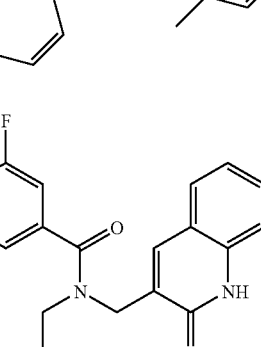 | B | D |
| NYAD-S118 | 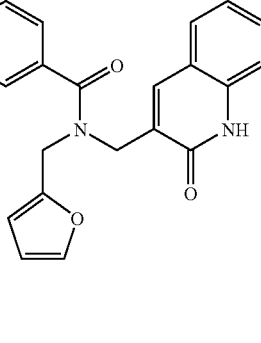 | A | D |

TABLE 1-continued
| Chemical Compound | Structure | IC$_{50}$ (μM)[1] | CC$_{50}$ (μM)[2] |
|---|---|---|---|
| NYAD-S121 | 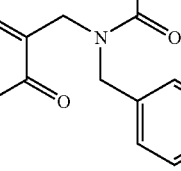 | A | D |
| NYAD-S122 | 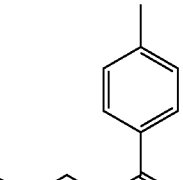 | A | C |
| NYAD-S6-4 | 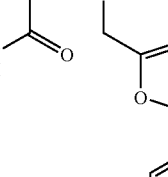 | A | D |
| NYAD-S6-6 | 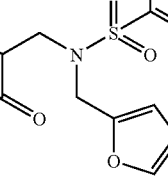 | A | D |
| NYAD-S6-8 | 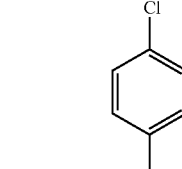 | A | D |

TABLE 1-continued

| Chemical Compound | Structure | IC$_{50}$ (μM)[1] | CC$_{50}$ (μM)[2] |
|---|---|---|---|
| NYAD-S6-10 | 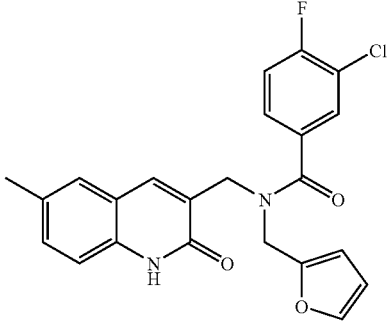 | A | D |
| NYAD-S6-19 | 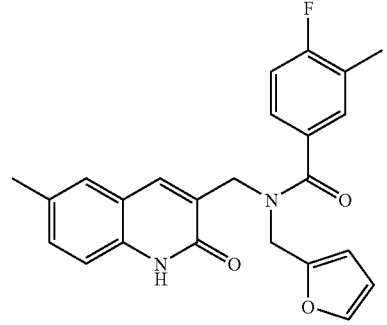 | A | D |
| NYAD-S6-21 | 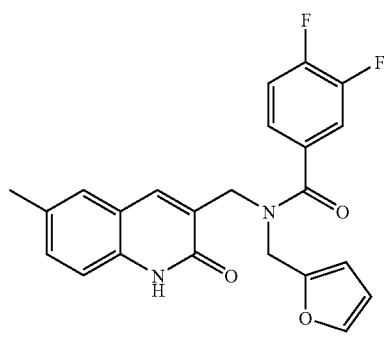 | A | D |

[1] A, IC$_{50}$ < 10 μM; B, IC$_{50}$ > 10 μM
[2] C, CC$_{50}$ < 10 μM; D, CC$_{50}$ > 10 μM

The various substituents and variables for the compounds of formula II are defined as follows:

$R_1$ is a moiety selected from the group consisting of hydrogen, substituted or unsubstituted ($C_{1-6}$)alkyl, substituted or unsubstituted ($C_{1-6}$)alkoxy, hydroxyl, hydroxy alkyl, halogen, nitrile, nitro, amino, sulphonyl, sulphonamido.

$R_2$ is a moiety selected from the group consisting of substituted or unsubstituted ($C_{1-6}$)alkyl, substituted or unsubstituted ($C_{1-6}$)alkoxy, carboxyl, alkyl amino sulphonyl, substituted or unsubstituted aryl amino sulphonyl, substituted or unsubstituted phenyl, substituted or unsubstituted benzyl, substituted or unsubstituted benzyloxy, substituted or unsubstituted alkyl phenyl, substituted or unsubstituted aminophenyl, cycloalkyl, substituted or unsubstituted aryl, substituted or unsubstituted heterocycle, and substituted or unsubstituted alkyl heterocycle.

A, V, W, X and Y are independently selected from CR$_3$ or N, wherein R$_3$ is a moiety selected from the group consisting of hydrogen, ($C_{1-6}$)alkyl, substituted or unsubstituted ($C_{1-6}$)alkyl, substituted or unsubstituted ($C_{1-6}$)alkoxy, hydroxyl, hydroxy alkyl, halogen, nitrile, amino, nitro.

Table 2 exemplifies some embodiments of formula II and includes the compound's corresponding IC$_{50}$ and CC$_{50}$ data. Compounds of formula II are not limited to those illustrated in Table 2.

TABLE 2
| Chemical Compound | Structure | IC$_{50}$ (µM)[1] | CC$_{50}$ (µM)[1] |
|---|---|---|---|
| NYAD-S8 | 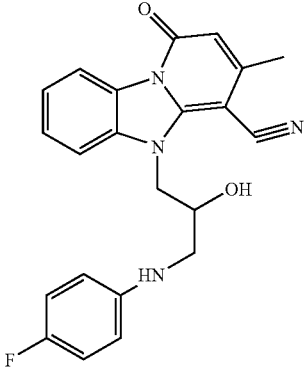 | B | D |
| NYAD-S9 | 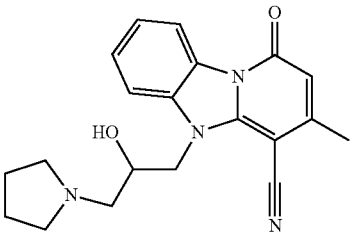 | B | D |
| NYAD-S10 | 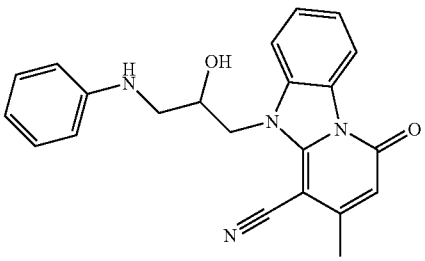 | B | D |
| NYAD-S11 | 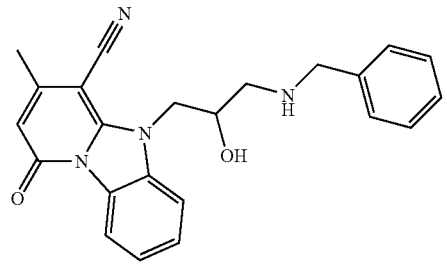 | B | D |
| NYAD-S12 | 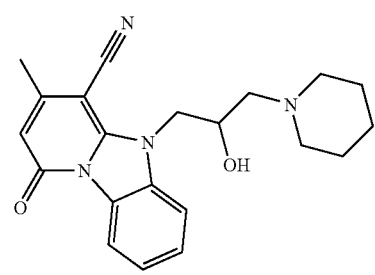 | B | D |

TABLE 2-continued

| Chemical Compound | Structure | IC$_{50}$ (μM)[1] | CC$_{50}$ (μM)[1] |
|---|---|---|---|
| NYAD-S13 | 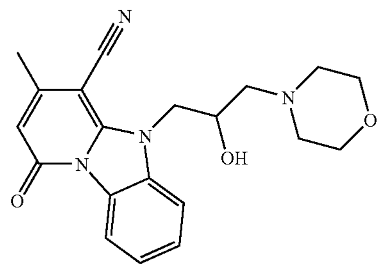 | B | D |
| NYAD-S14 | 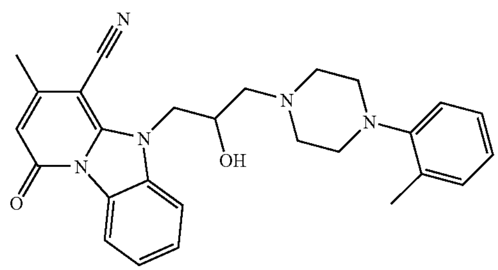 | B | D |
| NYAD-S15 | 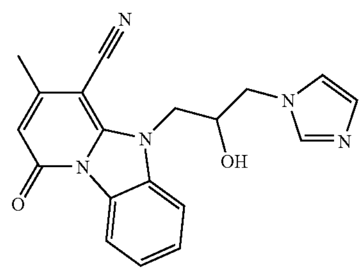 | B | D |
| NYAD-S16 | 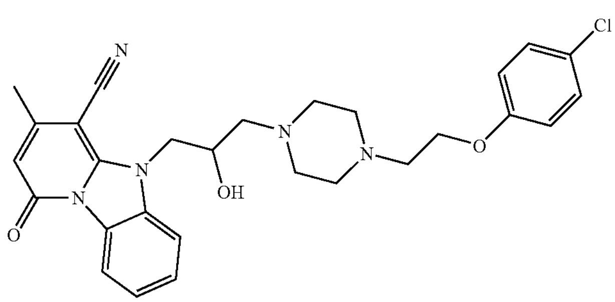 | A | D |
| NYAD-S17 | 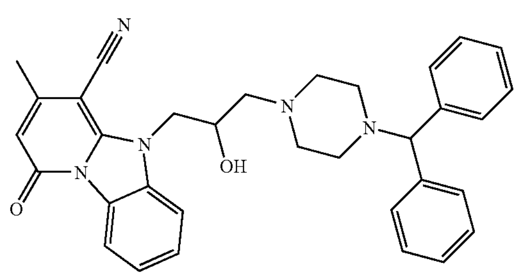 | A | D |

TABLE 2-continued
| Chemical Compound | Structure | IC$_{50}$ (μM)[1] | CC$_{50}$ (μM)[1] |
|---|---|---|---|
| NYAD-S18 | 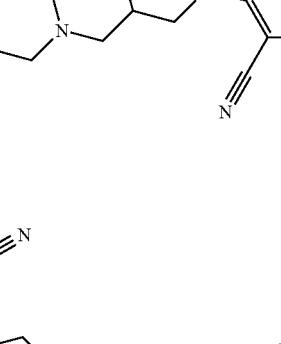 | B | D |
| NYAD-S19 | 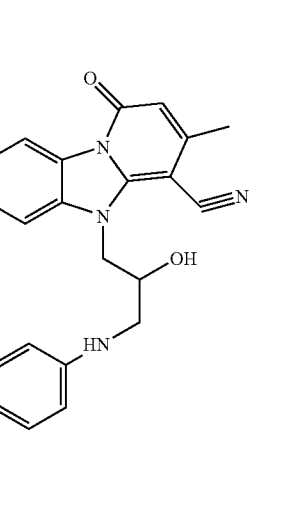 | B | D |
| NYAD-S52 | 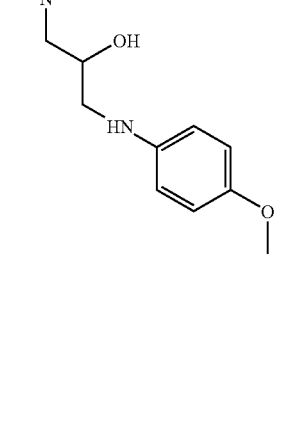 | B | D |
| NYAD-S53 | 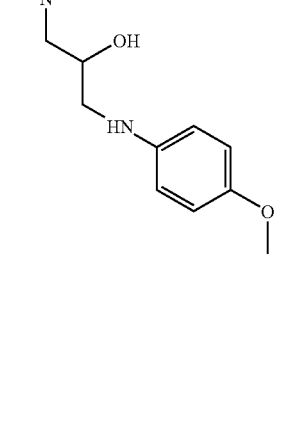 | B | D |

TABLE 2-continued

| Chemical Compound | Structure | IC$_{50}$ (μM)[1] | CC$_{50}$ (μM)[1] |
|---|---|---|---|
| NYAD-S54 | 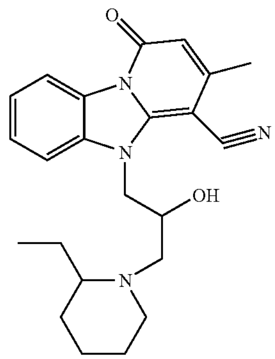 | B | D |
| NYAD-S55 | 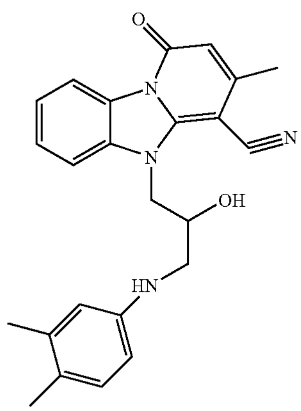 | B | D |
| NYAD-S56 | 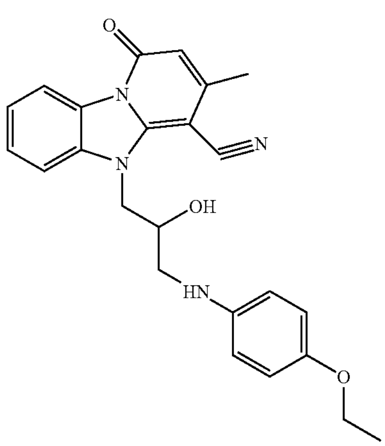 | B | D |

TABLE 2-continued
| Chemical Compound | Structure | IC$_{50}$ (μM)[1] | CC$_{50}$ (μM)[1] |
|---|---|---|---|
| NYAD-S57 | 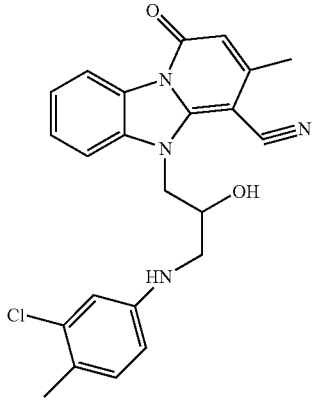 | B | D |
| NYAD-S58 | 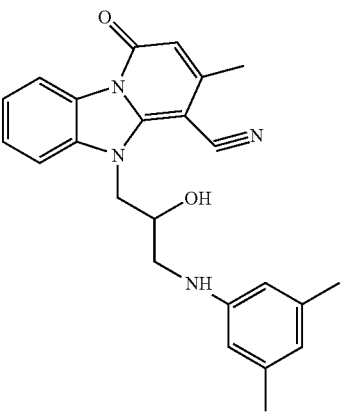 | B | D |
| NYAD-S59 | 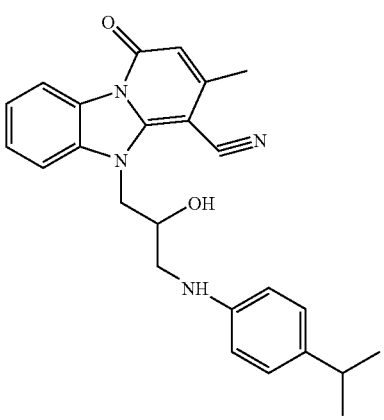 | A | C |

TABLE 2-continued
| Chemical Compound | Structure | IC$_{50}$ (μM)[1] | CC$_{50}$ (μM)[1] |
|---|---|---|---|
| NYAD-S60 | 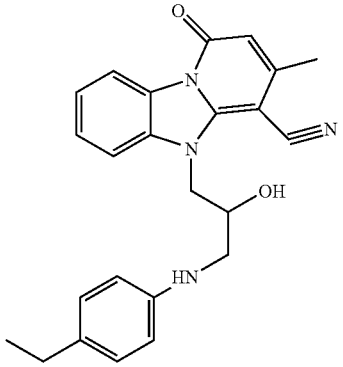 | B | C |
| NYAD-S62 | 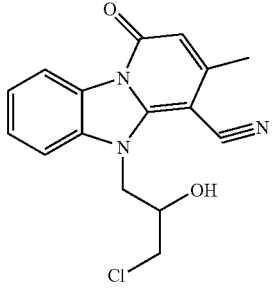 | B | D |
| NYAD-S63 | 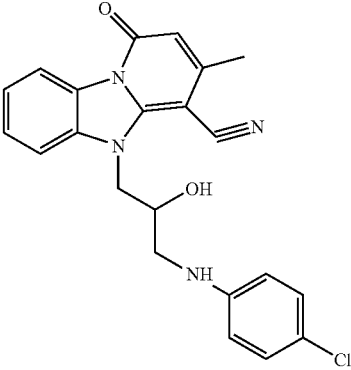 | B | D |
| NYAD-S64 | 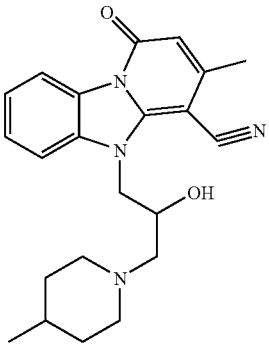 | B | D |

TABLE 2-continued

| Chemical Compound | Structure | IC$_{50}$ (μM)[1] | CC$_{50}$ (μM)[1] |
|---|---|---|---|
| NYAD-S65 | 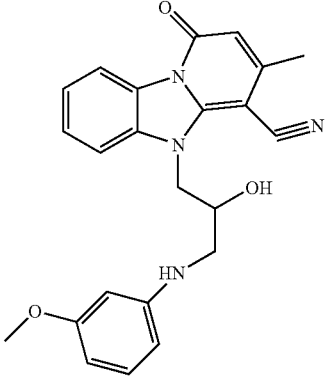 | B | D |

[1] A, IC$_{50}$ < 10 μM; B, IC$_{50}$ > 10 μM
[1] C, CC$_{50}$ < 10 μM; D, CC$_{50}$ > 10 μM

Figure 1B:
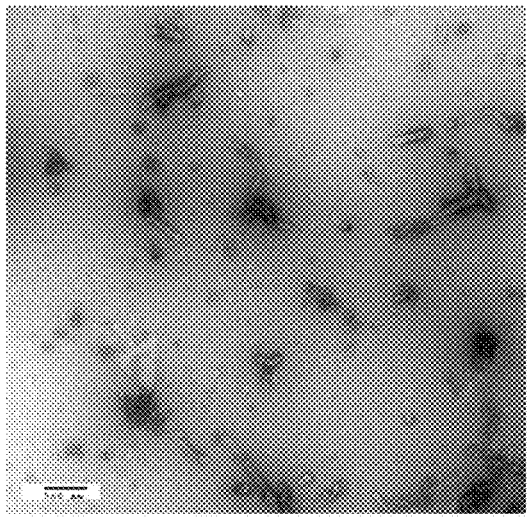
Figure 1C:
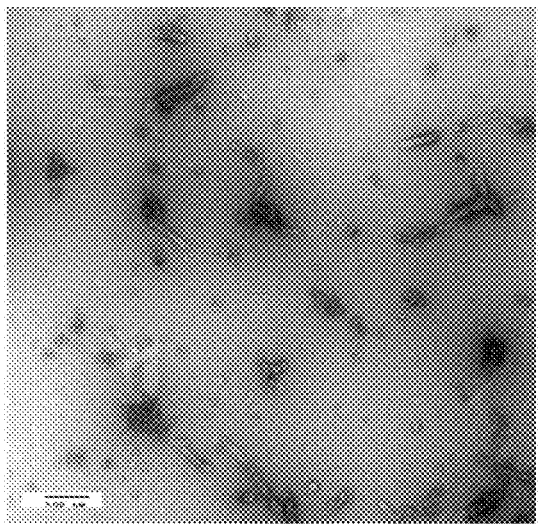
Figure 1D:
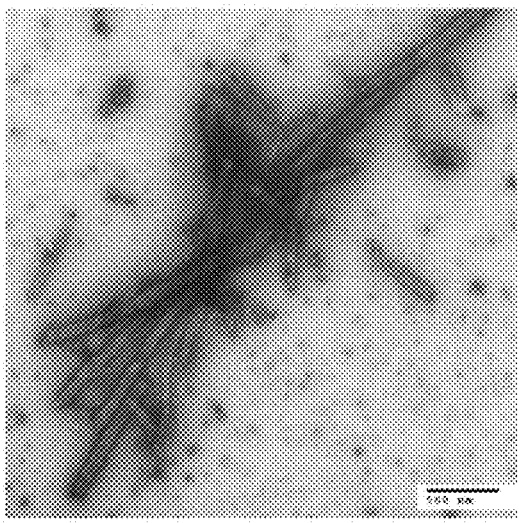
Figure 1E:
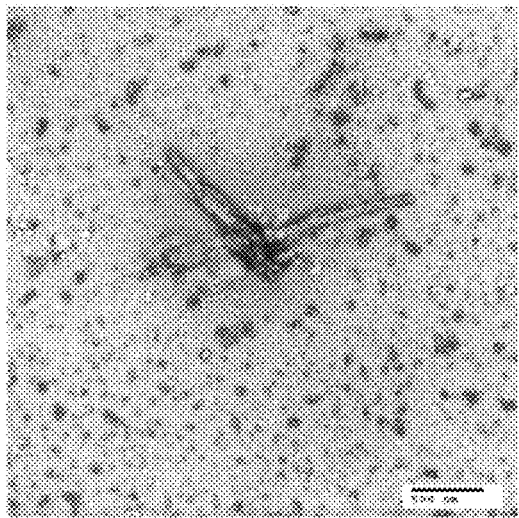
Figure 1F:
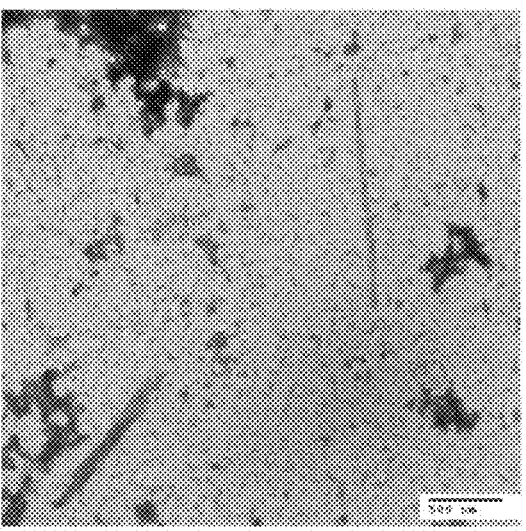
Figure 1G:
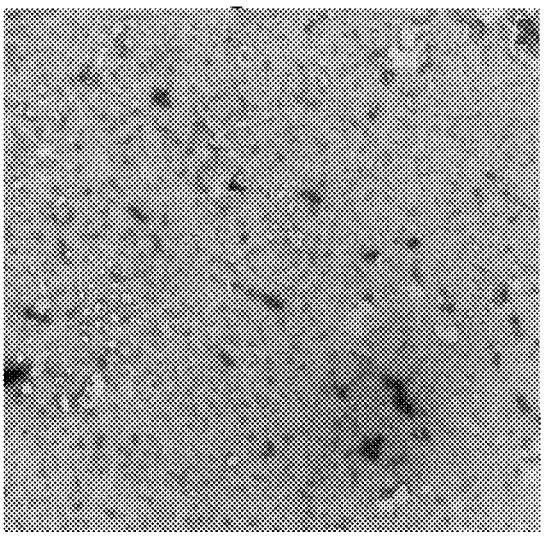

The present disclosure provides small molecule HIV inhibitors useful for prevention and/or treatment of HIV infections and/or associated diseases, disorders and conditions. More particularly, the pharmaceutical compositions presently disclosed are useful for disrupting HIV assembly and replication in cell culture and in cell-free environments. For example, FIGS. 1A-C illustrate the assembly of CA protein in the absence and presence of NYAD-S6. FIG. 1A illustrates CA protein assembly with no compound present; FIG. 1B illustrates CA protein assembly with 0.5-fold molar equivalent of NYAD-S6; and FIG. 1C illustrates CA protein assembly in the presence of 1-fold molar equivalent of NYAD-S6. As apparent from the Figures, the presence of NYAD-S6 greatly reduces the assembly of CA proteins. FIGS. 1D-G illustrate the assembly of CA protein in the absence or presence of NYAD-S8.

Figure 2A:
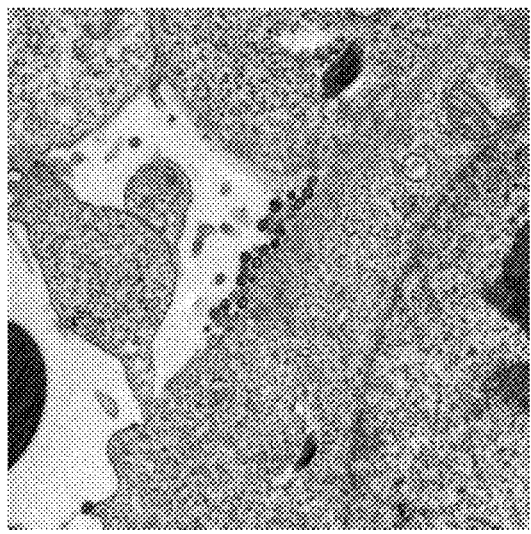
FIGS. 2A-D illustrates the effects of NYAD-S6 in a cell-based assay on disruption of formation of mature particles of HIV-1.
Figure 2B:
Figure 2C:
Figure 2D:
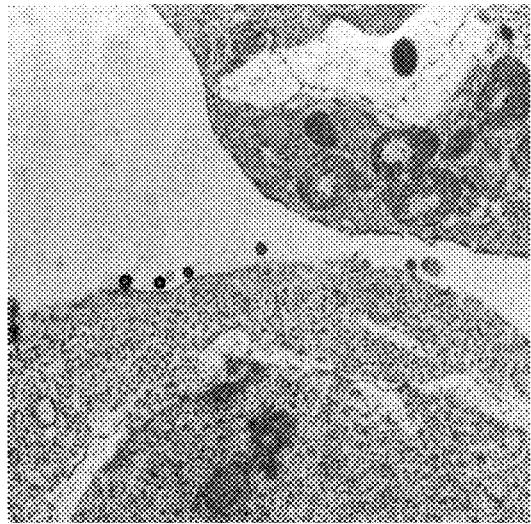

In another example, FIGS. 2A-D illustrate cell-based disruption of mature particle formation in the absence and presence of NYAD-S6. FIG. 2A is the control and depicts mature particle formation without NYAD-S6. FIGS. 2B, 2C and 2D illustrate mature particle formation in the presence of 0.4 μM, 2 μM and 10 μM of NYAD-S6, respectively. FIGS. 2A-D clearly illustrate a dramatic decrease in mature particle formation in the presence of NYAD-S6.

The pharmaceutical compositions herein disclosed comprise a therapeutically effective amount of HIV-1 small molecule inhibitors formulated for administration to a subject at risk of infection with HIV or to a patient suffering from or susceptible to an HIV infection and/or an associated disease, disorder or condition. Some of the disclosed compositions include at least one pharmaceutically acceptable excipient and may optionally include at least one additional therapeutically active agent.

The disclosed small molecule inhibitors may be administered in free form or, where appropriate, as a pharmaceutically acceptable derivative thereof. In some embodiments, the disclosed compounds are administered in a salt form; in other embodiments, the compounds are administered in an ester or prodrug form.

Appropriate excipients for use in the present pharmaceutical compositions may include, for example, one or more carriers, binders, fillers, vehicles, disintegrants, surfactants, dispersion or suspension aids, thickening or emulsifying agents, isotonic agents, preservatives, lubricants, and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. This document is incorporated herein by reference in its entirety.

Some of the disclosed compounds can comprise one or more asymmetric (chiral) centers, and thus can exist in various isomeric forms. The disclosed compounds and pharmaceutical compositions thereof may be in the form of an individual enantiomer, diastereomer, geometric isomer, or optical isomer, or may be in the form of a mixture of stereoisomers, and pharmaceutically acceptable salts, hydrates, and prodrugs thereof. In certain embodiments, the compounds of the present disclosure are tautomeric compounds. In other embodiments, mixtures of stereoisomers or diastereomers may be provided, e.g. racemic mixtures. In other embodiments, compounds may have one or more double bonds that can exist as either the Z or E isomer. The compounds and compositions of this disclosure also encompass pharmaceutically acceptable derivatives thereof, comprising one or more pharmaceutically acceptable excipients or additives.

The disclosed compositions may be formulated for any desirable route of delivery including, but not limited to, parenteral, intravenous, intradermal, subcutaneous, oral, inhalative, transdermal, topical, transmucosal, rectal, interacisternal, intravaginal, intraperitoneal, bucal and intraocular.

In certain aspects, parenteral, intradermal or subcutaneous formulations may be sterile injectable aqueous or oleaginous suspensions. Acceptable vehicles, solutions, suspensions and solvents may include, but are not limited to, water or other sterile diluent; saline; Ringer's solution; sodium chloride; fixed oils such as mono- or diglycerides; fatty acids such as oleic acid; polyethylene glycols; glycerine; propylene glycol or other synthetic solvents; antibacterial agents such as benzyl alcohol; antioxidants such as ascorbic acid; chelating agents such as ethylenediaminetetraacetic acid; buffers such as acetates, citrates or phosphates; and agents for the adjustment of tonicity such as sodium chloride or dextrose.

Solutions or suspensions used for parenteral, intradermal, or subcutaneous application may include one or more of the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation may be enclosed in ampoules, disposable syringes or multiple dose vials made of glass or plastic.

Pharmaceutical compositions suitable for injectable use may include sterile aqueous solutions or dispersions and sterile powders for the extemporaneous preparation of sterile injectable solutions or dispersion. For intravenous administration, suitable carriers include, but are not limited to, saline, bacteriostatic water, CREMOPHOR EL® (BASF, Parsippany, N.J.) or phosphate buffered saline (PBS). The solvent or dispersion medium may contain, for example, water, ethanol, polyol (for example, glycerol, propylene glycol, and liquid polyetheylene glycol, and the like), and suitable mixtures thereof. Proper fluidity can be maintained, for example, by the use of a coating such as lecithin, by the maintenance of the requited particle size in the case of dispersion and by the use of surfactants. Preventing growth of microorganisms can be achieved by various antibacterial and antifungal agents, for example, parabens, chlorobutanol, phenol, ascorbic acid, thimerosal, and the like. The composition may also include isotonic agents such as, for example, sugars; polyalcohols such as mannitol; sorbitol; or sodium chloride. Prolonged absorption of injectable compositions can be enhanced by addition of an agent which delays absorption, such as, for example, aluminum monostearate or gelatin.

Oral compositions may include an inert diluent or an edible carrier. They may be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or sterites; a glidant such as colloidal silicon dioxide; a sweetening agent such as sucrose or saccharin; or a flavoring agent such as peppermint, methyl salicylate, or orange flavoring.

Systemic administration may be by transmucosal or transdermal means. For transmucosal or transdermal administration, penetrants may be used. Such penetrants are generally known in the art, and include, for example, detergents, bile salts, and fusidic acid derivatives. Transdermal administration may include a bioactive agent and may be formulated into ointments, salves, gels, or creams as generally known in the art. Transmucosal administration may be accomplished through the use of nasal sprays or suppositories.

The disclosed HIV-1 small molecule inhibitors are useful in treating HIV-1 infections and/or associated diseases, disorders and conditions. The pharmaceutical compositions comprising at least one small molecule inhibitor may be administered to individuals suffering from or susceptible to HIV-1 infection.

The pharmaceutical compositions comprising the small molecule inhibitors may be administered in a therapeutically effective amount, according to an appropriate dosing regiment. As understood by a skilled artisan, an exact amount required may vary from subject to subject, depending on a subject's species, age and general condition, the severity of the infection, the particular agent(s) and the mode of administration. In some embodiments, about 0.001 mg/kg to about 50 mg/kg, of the pharmaceutical composition based on the subject's body weight is administered, one or more times a day, to obtain the desired therapeutic effect. In other embodiments, about 1 mg/kg to about 25 mg/kg, of the pharmaceutical composition based on the subject's body weight is administered, one or more times a day, to obtain the desired therapeutic effect.

A total daily dosage of the compounds and pharmaceutical compositions can be determined by the attending physician within the scope of sound medical judgment. A specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compounds and compositions may also be employed in combination therapies. That is, the compounds and pharmaceutically acceptable compositions presently disclosed can be administered concurrently with, prior to, or subsequent to, at least one other desired composition, therapeutic, treatment or medical procedure. A particular combination of therapies administered can be determined by an attending physician and can take into account compatibility of treatments and desired therapeutic effect to be achieved. It will be appreciated that therapeutically active agents utilized in combination may be administered together in a single composition, treatment or procedure, or alternatively may be administered separately.

For example, pharmaceutical compositions comprising the disclosed small molecule inhibitors may be administered in combination with at least one other HIV inhibitors including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors include, but are not limited to, abacavir (ABC; ZIAGEN®), didanosine (dideoxyinosine (ddI); VIDEX®), lamivudine (3TC; EPIVIR®), stavudine (d4T; ZERIT®, ZERIT XR®), zalcitabine (dideoxycytidine (ddC); HIVID®), zidovudine (ZDV, formerly known as azidothymidine (AZT); RETROVIR®), abacavir, zidovudine, and lamivudine (TRIZIVIR®), zidovudine and lamivudine (COMBIVIR®), and emtricitabine (EMTRIVA®). Nucleotide reverse transcriptase inhibitors include tenofovir disoproxil fumarate (VIREAD®). Non-nucleoside reverse transcriptase inhibitors for HIV include, but are not limited to, nevirapine (VIRAMUNE®), delavirdine mesylate (RESCRIPTOR®), and efavirenz (SUSTIVA®).

Protease inhibitors (PIs) for HIV include amprenavir (AGENERASE®), saquinavir mesylate (FORTOVASE®, INVIRASE®), ritonavir (NORVIR®), indinavir sulfate (CRIXIVAN®), nelfmavir mesylate (VIRACEPT®), lopinavir and ritonavir (KALETRA®), atazanavir (REYATAZ®), and fosamprenavir (LEXIVA®). Atazanavir and fosamprenavir (LEXIVA®) are new protease inhibitors that were recently approved by the U.S. Food and Drug Administration (FDA) for treating HIV-1 infection (see atazanavir (Reyataz) and emtricitabine (Emtriva) for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

Fusion inhibitors prevent fusion between the virus and the cell from occurring, and therefore, prevent HIV infection and multiplication. Fusion inhibitors include, but are not limited to, enfuvirtide (FUZEON®), Lalezari et al., New England J. Med., 348:2175-2185 (2003); and maraviroc (SELZENTRY®, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS®, Merck); and elvitegravir (GS 9137, Gilead Sciences).

Alternatively or additionally, the small molecule inhibitors may be administered in combination with one or more anti-infective agents (e.g., antibiotics, etc.), pain relievers, or other agents intended to address symptoms of one or more diseases, disorders, or conditions commonly found in immunocompromised individuals but not directly caused by HIV.

Example 1

Electron Microscopy to Study Inhibition of In Vitro Assembly and Maturation

In vitro assembly was studied in both a cell-free and a cell based system. The cell-free systems were set up as described (Huseby et al., Assembly of human immunodeficiency virus precursor gag proteins; J. Biol Chem, 280:17664-17670 (2005); Ganser-Pornillos et al., Assembly properties of the human immunodeficiency virus type-1 CA protein; J. Virol, 78:2545-2552 (2004); and Gross et al., In vitro assembly properties of purified bacterially expressed capsid proteins of human immunodeficiency virus; Eur. J. Biochem., 249:592-600 (1997)) with minor modifications. 50 mM $Na_2HPO_4$, pH 8.0 was used as the dialysis buffer. The buffer used for assembly studies also contained 1.2 M NaCl and 100 or 500-Da-MWCO dialysis tubes (SPECTRA®/Por) were used for the dialysis of peptides. Briefly, stock proteins were adjusted to the appropriate concentration (50 µM for CA proteins) in $Na_2HPO_4$ buffer at pH 8.0. After incubation with varied doses of Compounds NYAD-S6 and NYAD-S8 for 30 minutes at 4° C., the samples were dialyzed overnight in $Na_2HPO_4$ buffer at pH 8.0 containing 1.2 M NaCl at 4° C. Negative staining was used to check the assembly. Carbon-coated copper grids (200 mesh size; EM Sciences) were treated with 20 µL of poly-L-lysine (1 mg/mL; Sigma) for 2 minutes. 20 microliters of reaction solution was placed onto the grid for 2 minutes. Spotted grids were then stained with 30 µL of uranyl acetate solution for 2 minutes. Excess stain was removed and grids were air-dried. Specimens were examined with a Philips EM410 electron microscope.

Purified CA protein was expressed and tube-shaped particles were obtained (FIG. 1). Treatment with NYAD-S6 and NYAD-S8 resulted in dose-dependent disruption of the mature-like particles. After incubation with 0.5-fold molar equivalents of NYAD-S6, the integrity of tube-like particles was greatly damaged (FIG. 1B). After incubation with 1-fold molar equivalents of NYAD-S6, the assembly of tube-shaped particles was completely blocked (FIG. 1C). Similarly, after incubation with 0.5-fold and 1-fold molar equivalents of NYAD-S8, the integrity of tube-like particles was greatly damaged (FIGS. 1E and F). After incubation with 3-fold molar equivalents of NYAD-S8, the assembly of tube-shaped particles was completely blocked (FIG. 1G).

In the cell-based system, the impact of NYAD-S6 on virus-like particle (VLP) release and morphology was analyzed by electron microscopy one day post-transfection with plasmid encoding Gag-Pol. Forty thousand 293 T cells were seeded per well in a 6-well plate on the day before transfection. Cells were washed twice, 4 hours post-transfection and incubated with complete culture medium in the presence or absence of NYAD-S6 at different concentrations for another 20 hours. The cells were then fixed in 3% glutaraldehyde in 100 mM sodium cacodylate for 1 hour and post-fixed in 1% $OsO_4$ in 100 mM sodium cacodylate for another 1 hour. Specimens were then dehydrated through graded series of ethanol solutions and embedded in EPON® media. After staining with uranyl acetate and lead citrate, ultra-thin sections were examined under a Philips EM410 electron microscope.

In the case of untreated cells transfected with a Gag-Pol expression vector, a large number of mature particles containing electron-dense core structures were found (FIG. 2A). When Gag-Pol expressing cells were treated with 0.4, 2 and 10 µM of NYAD-S6, formation of electron-dense core structures was markedly inhibited (FIGS. 2B, 2C and 2D). This data confirm that NYAD-S6 targets capsid and impairs proper particle assembly and maturation in Gag-Pol expressing cells.

Example 2

Inhibition of HIV-1 Infectivity

The inhibitory activity of NYAD-S6, NYAD-S8 and their analogs on infection by laboratory-adapted HIV-1 strains was determined as previously described (Jiang et al., Enhancement of human immunodeficiency virus type-1 infection by antisera to peptides from the envelope glycoproteins gp120/gp41; J. Exp. Med., 174:1557-1563 (1991)) with minor modifications. AZT was used as a positive control in the infectivity assays. In brief, $1 \times 10^4$ MT-2 cells (lymphocytes) were infected with HIV-1 at 100 $TCID_{50}$ (50% tissue culture infective dose, 0.01 MOI [multiplicity of infection]) in 200 µL RPMI 1640 medium containing 10% FBS in the presence or absence of small molecules at graded concentrations overnight. The culture supernatants were then removed and fresh media containing freshly prepared test compounds were added. On the fourth day post-infection, 100 µL of culture supernatants were collected from each well, mixed with equal volume of 5% TRITON X-100® and tested for p24 antigen by ELISA®. The $IC_{50}$ values were calculated by the GraphPad Prism software (GraphPad Software®, Inc.) and the values were classified as $IC_{50}<10$ µM and $IC_{50}>10$ µM.

The inhibitory activity of selected potent small-molecule inhibitors, such as Compounds NYAD-S6, NYAD-S8 and NYAD-S17, on infection by primary HIV-1 isolates was determined as previously described (Jiang et al., N-substituted pyrrole derivatives as novel human immunodeficiency virus type-1 entry inhibitors that interfere with the gp41 six-helix bundle formation and block virus fusion; Antimicrob. Agents Chemotherapy, 48:4349-4359, 2004). Peripheral blood mononuclear cells (PBMCs) were isolated from the blood of healthy donors by standard density gradient centrifugation using Histopaque-1077 (Sigma). The cells were cultured at 37° C. for 2 hours. Nonadherent cells were collected and resuspended at $5 \times 10^6$ cells/ml RPMI-1640 medium containing 10% FBS, 5 µg/ml PHA, and 100 U/ml IL-2 (Sigma), followed by incubation at 37° C. for 3 days. The PHA-stimulated cells ($5 \times 10^4$ cells/well) were infected with primary HIV-1 isolates at 500 $TCID_{50}$ (0.01 MOI) in the absence or presence of small molecule inhibitor at graded concentrations. Culture media were changed every 3 days and replaced with fresh media containing freshly prepared inhibitor. The supernatants were collected 7 days post-infection and tested for p24 antigen by ELISA. The inhibition of p24 production in PBMC was measured over a range of concentrations and the concentration required to inhibit 50% ($IC_{50}$) of the p24 production was calculated by the GraphPad Prism software.

The inhibitory activity of NYAD-S6 and its analogs against HIV-1 strain has been presented in Table 1. The inhibitory activity of NYAD-S8 and its analogs has been listed in Table 2. The molecules in Tables 1 and 2 include the calculated $IC_{50}$ values and use "A" to denote $IC_{50} < 10$ μM and "B" to denote $IC_{50} > 10$ μM.

Compounds NYAD-S6, NYAD-S8 and NYAD-S17, an analog of NYAD-S8, identified by similarity search, were also tested against a broad range of HIV-1 laboratory-adapted and primary isolates, including one RT-inhibitor-resistant isolate and one protease-inhibitor-resistant isolate. These compounds showed consistently potent activity (Table 3). The molecules in Tables 3 include the calculated $IC_{50}$ values and use "$A_1$" to denote $IC_{50} < 10$ μM and "$B_1$" to denote $IC_{50} > 10$ μM and "$C_1$" to denote $CC_{50} < 50$ μM and "$D_1$" to denote $IC_{50} > 50$ μM.

TABLE 3

Antiviral activity ($IC_{50}$) and cytotoxicity ($CC_{50}$) of Compounds NYAD-S6, NYAD-S8 and NYAD-S17 in laboratory-adapted and primary HIV-1 isolates

| HIV-1 virus | Subtype | Cell Type | Co-receptor | [1]$IC_{50}$ (μM ± SD) NYAD-S6 | NYAD-S8 | NYAD-S17 |
|---|---|---|---|---|---|---|
| Laboratory Strains | | | | | | |
| IIIB | B | MT-2 | X4 | $A_1$ | $B_1$ | $A_1$ |
| MN | B | MT-2 | X4 | $A_1$ | $A_1$ | $A_1$ |
| SF2 | B | MT-2 | R5X4 | $A_1$ | $A_1$ | $A_1$ |
| RF | B | MT-2 | X4 | $A_1$ | $A_1$ | $A_1$ |
| BaL | B | PBMC | R5 | $A_1$ | $A_1$ | $A_1$ |
| RT-Resistant Isolate | | | | | | |
| AZT-R | B | MT-2 | X4 | $A_1$ | $A_1$ | $A_1$ |
| Protease Resistant Isolate | | | | | | |
| HIV-1$_{RF/L-323-12-3}$ | B | MT-2 | X4 | $A_1$ | $A_1$ | ND |
| Primary isolates | | | | | | |
| 92US657 | B | PBMC | R5 | $A_1$ | $A_1$ | $A_1$ |
| 93IN101 | C | PBMC | R5 | $A_1$ | $A_1$ | $A_1$ |
| 93Br020 | F | PBMC | R5X4 | $A_1$ | $A_1$ | ND |
| RU570 | G | PBMC | R5 | $A_1$ | $A_1$ | $A_1$ |
| BCF02 | Group (O) | PBMC | R5 | $A_1$ | $B_1$ | $A_1$ |

| Small Molecules | [2]$CC_{50}$ (μM ± SD) in MT-2 | [2]$CC_{50}$ (μM) in PBMC |
|---|---|---|
| NYAD-S6 | $D_1$ | $D_1$ |
| NYAD-S8 | $D_1$ | $D_1$ |
| NYAD-S17 | $C_1$ | $C_1$ |

[1]$A_1 = IC_{50} < 10$ μM; $B_1 = IC_{50} > 10$ μM
[2]$C_1 = CC_{50} < 50$ μM; $D_1 = CC_{50} > 50$ μM
ND, Not determined Example 3

Cytotoxicity of Inhibitors

Cytotoxicity of small molecules in cultures with MT-2 cells and PBMC was measured by the tetrazolium hydroxide XTT (sodium 3'-(1-(phenylamino)-carbonyl)-3,4-tetrazolium-bis(4-methoxy-6-nitro) benzenesulfonic acid hydrate) cytotoxicity assay, as previously described (Jiang et al., 2004). Briefly, for MT-2 cells, 100 μL of small molecule at graded concentrations was added to an equal volume of cells ($5 \times 10^4$ cells/ml) in 96-well plates followed by incubation at 37° C. for 4 days, which ran parallel to the neutralization assay in MT-2 (except medium was added instead of virus). In the case of PBMC, $2.5 \times 10^5$ cells/mL were used and the cytotoxicity was measured after 7 days. After addition of XTT (PolySciences, Inc.), the soluble intracellular formazan was quantitated calorimetrically at 450 nm 4 hours later with a reference at 620 nm. The $CC_{50}$ values were calculated.

The cytotoxicity measurements of NYAD-S6 and its analogs have been presented in Table 1. The cytotoxicity measurements of NYAD-S8 and its analogs have been presented in Table 2. The molecules in Tables 1 and 2 include the calculated $CC_{50}$ values and use "C" to denote $CC_{50} < 10$ μM and "D" to denote $CC_{50} > 10$ μM.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for disrupting HIV assembly and replication comprising:
administering to a patient in need thereof a pharmaceutical composition comprising a pharmaceutically effective amount of a compound of formula I, or a pharmaceutically acceptable salt or ester thereof,

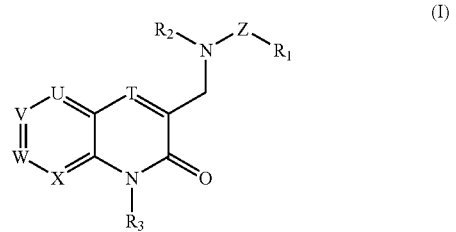

(I)

wherein $R_1$ is substituted or unsubstituted phenyl, or substituted or unsubstituted furanyl;
$R^2$ is substituted or unsubstituted benzyl, or substituted or unsubstituted alkyl furanyl;
$R_3$ is a moiety selected from the group consisting of H, and substituted or unsubstituted $(C_{1-6})$alkyl;

Z is C=O or C=S; and

T, U, V, W and X are independently selected from $CR_4$ or N, wherein $R_4$ is a moiety selected from the group consisting of hydrogen, substituted or unsubstituted $(C_{1-6})$ alkyl, substituted or unsubstituted $(C_{1-6})$alkoxy, hydroxyl alkyl, Cl, Br, and F;

disrupting HIV assembly and replication.

2. The method of claim 1, further comprising administering at least one additional therapeutic agent selected from the group consisting of reverse transcriptase inhibitors, protease inhibitors, fusion inhibitors, integrase inhibitors, chemokine receptor (CXCR4, CCR5) inhibitors, interleukin-2, hydroxyurea, monoclonal antibodies, and cytokines.

3. The method of claim 1, wherein said compound is selected from the group consisting of:

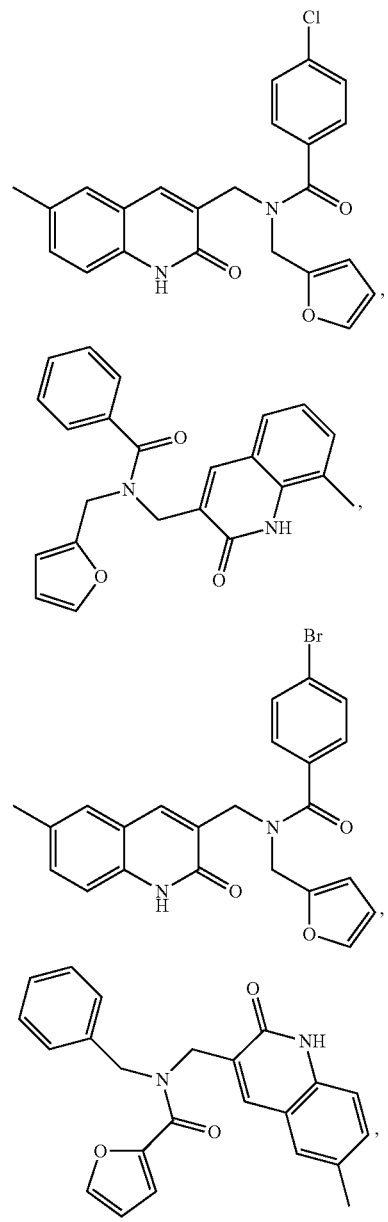

65
-continued
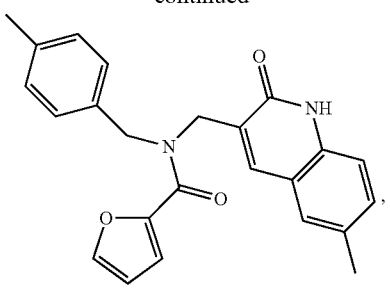
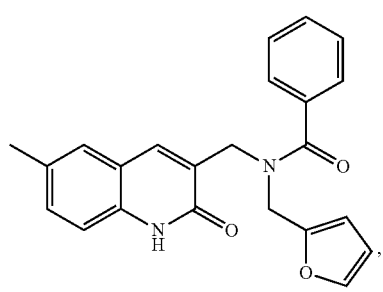
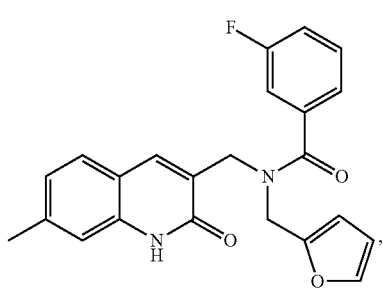
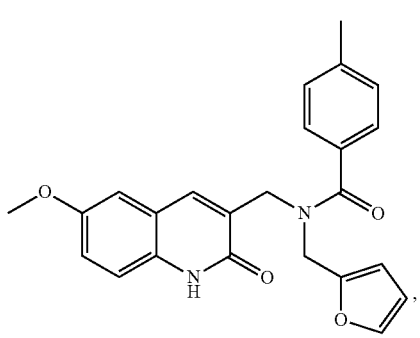
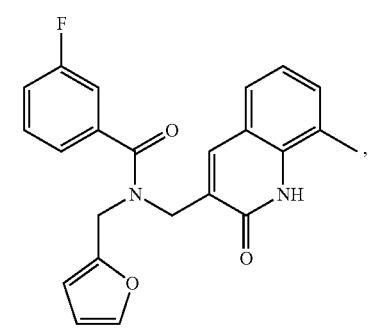
66
-continued
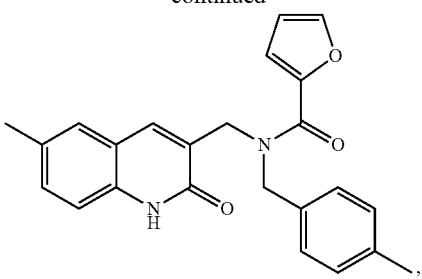
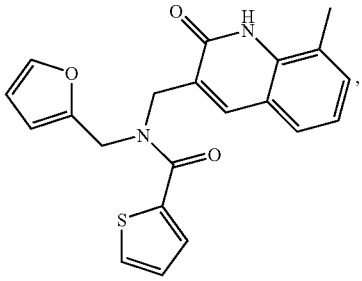
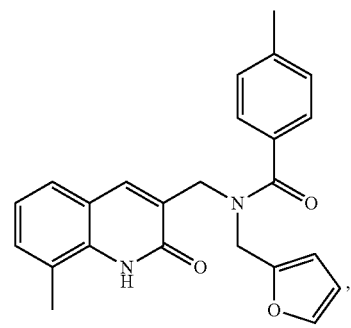
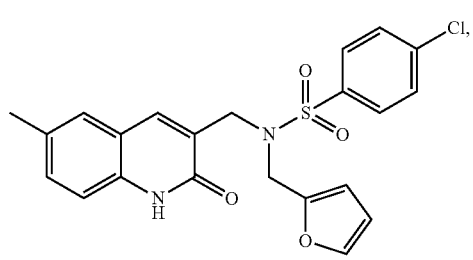

-continued
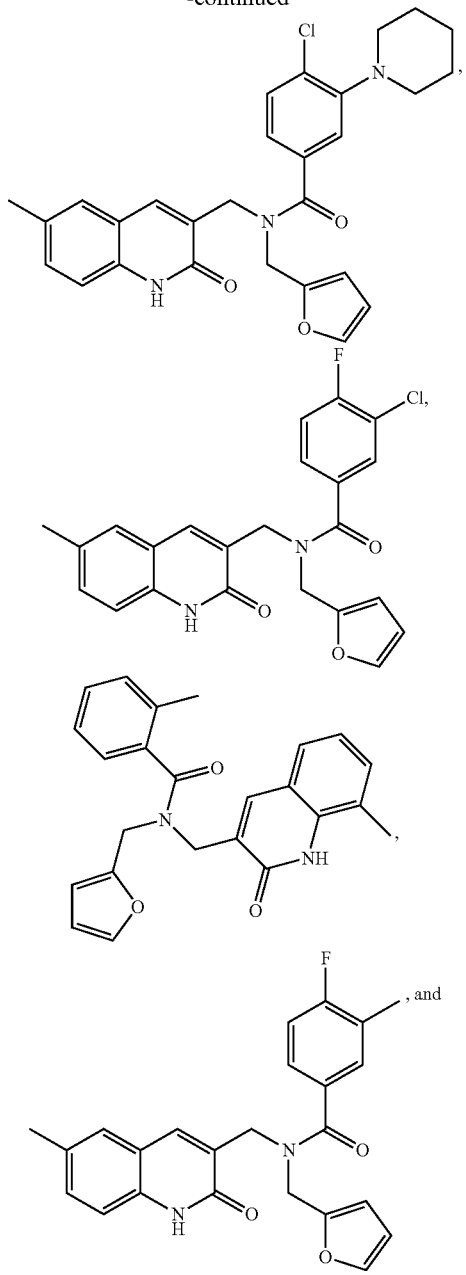
-continued
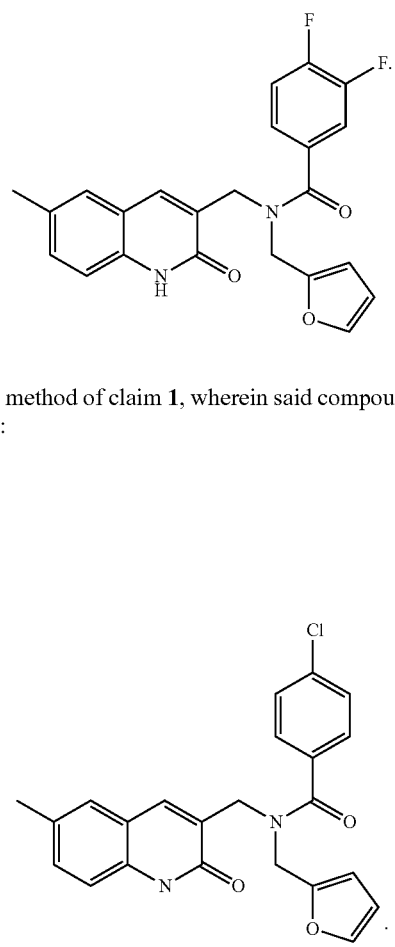
4. The method of claim 1, wherein said compound has the structure:
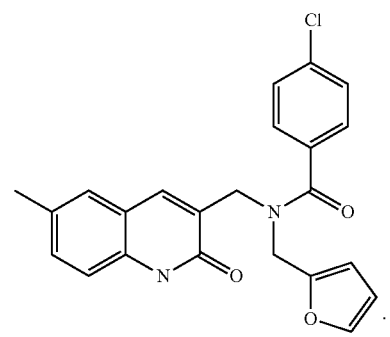
5. The method of claim 1, wherein said composition further comprises at least one pharmaceutically acceptable excipient.
6. The method of claim 1, wherein said composition further comprises at least one additional therapeutically active agent.
\* \* \* \* \*